US011781247B2

(12) United States Patent
Manucharyan et al.

(10) Patent No.: US 11,781,247 B2
(45) **Date of Patent: *Oct. 10, 2023**

(54) VARIABLE EPITOPE LIBRARY COMPOSITIONS AND METHODS OF THERAPEUTIC AND PROPHYLACTIC USE

(71) Applicant: Primex Clinical Laboratories, Inc., Van Nuys, CA (US)

(72) Inventors: Karen Manucharyan, Mexico City (MX); Gohar Gevorgyan, Mexico City (MX)

(73) Assignee: Primex Clinical Laboratories, Inc., Van Nuys, CA (US)

( * ) Notice: Subject to any disclaimer, the term of this patent is extended or adjusted under 35 U.S.C. 154(b) by 596 days.

This patent is subject to a terminal disclaimer.

(21) Appl. No.: 16/544,189

(22) Filed: Aug. 19, 2019

(65) Prior Publication Data

US 2019/0374625 A1 Dec. 12, 2019

Related U.S. Application Data

(63) Continuation of application No. 14/991,807, filed on Jan. 8, 2016, now Pat. No. 10,383,927.

(Continued)

(51) Int. Cl.
*C40B 30/06* (2006.01)
*A61K 39/00* (2006.01)

(52) U.S. Cl.
CPC ........ *C40B 30/06* (2013.01); *A61K 39/00115* (2018.08); *A61K 2039/572* (2013.01); *A61K 2039/80* (2018.08)

(58) Field of Classification Search
None
See application file for complete search history.

(56) References Cited

U.S. PATENT DOCUMENTS 7,118,874 B2 10/2006 Torres
8,029,797 B2 10/2011 Torres et al.

(Continued)

FOREIGN PATENT DOCUMENTS

WO 2004/031212 A1 4/2004
WO 2008/087216 A1 7/2008

OTHER PUBLICATIONS

Sarobe, et al., "Enhanced In Vitro Potency and In Vivo Immunogenicity of a CTL Epitope from Hepatitis C Virus Core Protein Following Amino Acid Replacement at Secondary LA-A2.1 Binding Positions," I Clin. Investigation, vol. 102 (6), pp. 1239-1248 (Sep. 1998).

(Continued)

*Primary Examiner* — Christian C Boesen
(74) *Attorney, Agent, or Firm* — Nutter McClennen & Fish LLP

(57) ABSTRACT

The present disclosure relates to compositions and methods for targeting antigenically variable pathogens and diseases. Embodiments of the present disclosure involve of the construction of variable epitope libraries (VELs) containing mutated versions of epitopes derived from antigens associated with various diseases for treating subjects in both therapeutic and prophylactic settings. The present disclosure also provides compositions and methods for the production of VELs based on CTL-derived epitopes of survivin, an oncogenic inhibitor-of-apoptosis. Given the large number of potential epitopes expressed in tumors, and the dynamic nature of the tumor epitope landscape, there is a need to develop compositions and methods for targeting various antigenic epitopes to counteract immune escape.

13 Claims, 7 Drawing Sheets
(7 of 7 Drawing Sheet(s) Filed in Color)

Specification includes a Sequence Listing.

Related U.S. Application Data

(60) Provisional application No. 62/101,874, filed on Jan. 9, 2015.

(56) References Cited

U.S. PATENT DOCUMENTS

| | | | |
|---|---|---|---|
| 10,383,927 | B2 | 8/2019 | Manucharyan et al. |
| 2003/0161809 | A1 | 8/2003 | Houston et al. |
| 2004/0086520 | A1 | 5/2004 | Diamond |
| 2005/0222383 | A1 | 10/2005 | Harris et al. |
| 2006/0153772 | A1 | 7/2006 | Jacobsen |
| 2007/0135618 | A1 | 6/2007 | Peakman et al. |
| 2016/0199471 | A1 | 7/2016 | Manucharyan et al. |

OTHER PUBLICATIONS

Siegel, et al., "Induction of antitumor immunity using survivn peptide-pulsed dendritic cells in a murine lymphoma model," British Journal of Haematology, vol. 122, pp. 911-914 (2003).
Sukati, et al., "Mapping helper T-cell epitopes on platelet membrane glycoprotein IIIa in chronic autoimmune thrombocytopenic purpura," Blood, The American Society of Hematology, US, vol. 109, No. 10, May 1, 2007, pp. 4528-4538.
Tamm et al., IAP Family Protein Survivn Inhibits Caspase Activity and Apoptosis Induced by Fas (CD95), Bax, Caspases, and Anticancer Drugs, Cancer Research, vol. 58, pp. 5315-5320 (1998).
Udaka, et al., "Decrypting the Structure of Major Histocompatibility Complex Class I-Restricted Cytotoxic T Lymphocyte Epitopes with Complex Peptide Libraries," I Exp. Med., vol. 181 (6), pp. 2097-2108 (Jun. 1995).
Woodberry, et al., "Immunogenicity of a Human Immunodeficiency Virus (HIV) Polytope Vaccine Containing Multiple HLA A2 HIV CD8+ Cytotoxic T-Cell Epitopes," I. Virol., vol. 73 (7), pp. 5320-5325 (Jul. 1999).
Wooldridge, et al., "A Single Autoimmune T Cell Receptor Recognizes More Than a Million Different Peptides," The Journal of Biological Chemistry vol. 287, No. 2, pp. 1168-1177 (2012).
Wu Ying Wan, et al., "Phage Display Particles Expressing Tumor-Specific Antigens Induce Preventive and Therapeutic Anti-Tumor Immunity in Murine P815 Model,"Int. I Cancer, vol. 98, pp. 748-753 (2002).
Zaremba, et al., "Identification of an Enhancer Agonist Cytotoxic T Lymphocyte Peptide from Human Carcinoembryonic Antigen," Cancer Research vol. 57, Issue 20, pp. 4570-4577 (1997).
Abdul-Alim, et al. "Conditional Superagonist CTL Ligands for the Promotion of Tumor-Specific CTL Responses," The Journal of Immunology, vol. 184, pp. 6514-6521 (2010).
Anderson D.E., et al. "Overcoming Original (Antigenic) Sin," Clinical Immunology, vol. 101 (2), pp. 152-157 (Nov. 2001).
Birnbaum, et al., "Deconstructing the peptide-MHC specificity of T cell recognition," Cell vol. 157, No. 5, pp. 1073-1087 (2014).
Borbulevych, et al., "Increased Immunogenicity of an Anchor-Modified Tumor Associated Antigen is Due to the Enhanced Stability of the Peptide/MHC Complex: Implications for Vaccine Design," The Journal of Immunology vol. 174, pp. 4812-4820 (2005).
Bryant, et al. "Class II MHC peptide loading by the professionals," Current Opinion in Immunology, vol. 16, pp. 96-102 (2004).
Buhrman, et al. "Augmenting Antitumor T-Cell Responses to Mimotope Vaccination by Boosting with Native Tumor Antigens," vol. 73, Issue 1, pp. 74-85 (2013).
Buhrman, et al. "Improving Antigenic Peptide Vaccines for Cancer Immunotherapy Using a Dominant Tumor-specific T Cell Receptor," The Journal of Biological Chemistry vol. 288, No. 46, pp. 33213-33225 (2013).
Burton, et al., "Why do we not have an HIV vaccine and how can we make one," Nature Medicine, vol. 4 (5), pp. 495-498 (1998).
Carlos, et al., "Immunogenicity of a Vaccine Preparation Representing the Variable Regions of the HIV Type I Envelope Glycoprotein," AIDS Research and Human Retroviruses, vol. 16 (2), pp. 153-161 (2000).
Castric, et al., "Peptide epitope mapping in vaccine development: Introduction," Journal of Industrial Microbiology & Biotechnology, vol. 19, pp. 56-57 (1997).
Clark, et al., "Bacterial viruses as human vaccines?," Expert Rev. Vaccines, vol. 3 (4), pp. 463-476 (Aug. 2004) [Abstract only].
De Oliveira E, et al., "Analysis of the immune response against mixotope peptide libraries from a main antigenic site of foot-and-mouth disease virus," Vaccine, vol. 23, pp. 2647-2657 (2005).
Desrosiers, R.C., "Prospects for an AIDS vaccine," Nature Medicine, vol. 10 (3), pp. 221-223 (Mar. 2004).
Ekeruche-Makinde, et al. "T-cell Receptor-optimized Peptide Skewing of the T-cell Repertoire Can Enhance Antigen Targeting," The Journal of Biology Chemistry, vol. 287, No. 44, 2012, pp. 37269-37281.
European Search Report for Application No. 06738772.0-2405, dated May 17, 2010 (9 pages).
Extended European Search Report for Application No. 17858884.4, dated May 19, 2020 (7 pages).
Gallou, et al., "A general strategy to optimize immunogenicity of HLA-B*0702 restricted cryptic peptides from tumor associated antigens: Design of universal neo-antigen like tumor vaccines for HLA-B*0702 positive patients," Oncotarget, vol. 7, No. 37, pp. 59417-59428 (2016).
Gras, et al., "Allelic polymorphism in the T cell receptor and its impact on immune responses," J. Exp. Med. vol. 207, No. 7, pp. 1555-1567 (2010).
Hemmer, et al., "Probing degeneracy in T-cell recognition using peptide combinatorial libraries," Immunology Today, vol. 19 (4), pp. 163-168 (Apr. 1998).
Hengartner, et al., "Deletion of self-reactive T cells before entry into the thymus medulla," Nature vol. 336, pp. 388-390 (1988).
Hoppes, et al. "Altered Peptide Ligands Revisited: Vaccine Design through Chemically Modified HLA-A2-Restricted T Cell Epitopes," The Journal of Immunology, vol. 193, pp. 4803-4813 (2014).
Houghten, R.A., "The broad utility of soluble peptide libraries for drug discovery," Gene, vol. 137, pp. 7-11 (1993).
International Search Report and Written Opinion for Application No. PCT/US2006/009751, dated Apr. 3, 2007 (5 pages).
International Preliminary Report on Patentability for International Application No. PCT/US2006/009571, dated Sep. 18, 2007 (8 pages).
International Search Report and Written Opinion for International Application No. PCT/US2017/051845, dated Jan. 23, 2018 (16 pages).
International Preliminary Report on Patentability for International Application No. PCT/US2017/051845, dated Mar. 28, 2019 (7 pages).
Jordan, et al., "Peptide vaccines prevent tumor growth by activating T cells that respond to native tumor antigens," PNAS vol. 107, No. 7, pp. 4652-4657 (2010).
Kappler, et al., "T Cell Tolerance by Clonal Elimination in the Thymus," Cell, vol. 49, pp. 273-280 (1987).
La Rosa et al., "Enhanced immune activity of cytotoxic T-lymphocyte epitope analogs derived from positional scanning synthetic combinatorial libraries" Blood, vol. 97(6), pp. 1776-1786, Mar. 2001.
Le et al., "Gemcitabine directly inhibits myeloid derived suppressor cells in BALB/c mice bearing 4T1 mammary carcinoma and augments expansion of T cells from tumor-bearing mice," International Immunopharmacology, vol. 9, pp. 900-909 (2009).
Lipford, et al., "Peptide engineering allows cytotoxic T-cell vaccination against human papilloma virus tumor antigen, E6," Immunology, vol. 84, pp. 298-303 (1995).
Lipford, et al., "In vivo CTL induction with point-substituted ovalbumin peptides: immunogenicity correlates with peptide-induced MHC class I stability," Vaccine, vol. 13 (3), pp. 313-320 (1995).
Lundegaard, et al., "Major histocompatibility complex class I binding predictions as a tool in epitope discovery," Immunology 130, pp. 309-318 (2010).

(56) References Cited

OTHER PUBLICATIONS

Marchand, et al., "Tumor Regressions Observed In Patients with Metastatic Melanoma Treated with An Antigenic Peptide Encoded By Gene MA.GE-3 and Presented by I-ILA-A 1," Int. J. Cancer, vol. 80, pp. 219-230 (1999).
Marquez, et al., "Human Papillomavirus Immunogen That Provides Protective Tumor Immunity and Induces Tumor Regression," Viral Immunology, vol. 25 (2), pp. 141-152 (2012).
Matthews, et al., "Prospects for Development of a Vaccine Against I-ITIN-III-Related Disorders," Aids Res. And Hum. Retro., vol. 3, Supp. 1, pp. 197-206 (1987) [excerpt, 1 page].
McKinney, et al., "Recognition of Variant HIV-1 Epitopes from Diverse Viral Subtypes by Vaccine-Induced CTL," The Journal of Immunology, vol. 173 (3), pp. 1941-1950 (Aug. 1994).
McMahan,et al, "Relating TCR-peptide-MHC affinity to immunogenicity for the design of tumor vaccines," The Journal of Clinical Investigation, vol. 116, No. 9, pp. 2543-2551 (2006).
Meyer, et al., "Hypervariable Epitope Constructs Representing Variability in Envelope Glycoprotein of SW Induce a Broad Humoral Immune Response in Rabbits and Rhesus Macaques," Aids Research and Human Retroviruses, vol. 14 (9), pp. 751-760 (Jun. 1998).
Noedominguez-Romero, et al., "Variable epitope library carrying heavily mutated survivin-derived CTL epitope variants as a new class of efficient vaccine immunogen tested in a mouse model of breast cancer," Human Vaccines & Immunotherapeutics, vol. 10, Issue 11, pp. 3201-3213 (2014).
Okugawa, et al., "A novel human HER2-derived peptide homologous to the mouse Kd-restricted tumor rejection antigen can induce HLA-A24-restricted cytotoxic T lymphocytes in ovarian cancer patients and health individuals," Eur. J. Immunology. vol. 30, pp. 3338-3346 (2000).
Parkhurst, et al., "Improved induction of melanoma-reactive CTL with peptides from the melanoma antigen gp100 modified at HLA-A*0201-binding residues," The Journal of Immunology vol. 157, Issue 6, pp. 2539-2548 (1996).
Pedroz-Roldan et al., "Variable epitope library-based vaccines: Shooting moving targets," Molecular Immunology, vol. 47, pp. 270-282 (2009).
Pinilla, et al., "Combinatorial Peptide Libraries as an Alternative Approach to the Identification of Ligands for Tumor-reactive Cytolytic L Lymphocytes," Cancer Research, vol. 61, pp. 5153-5160 (Jul. 2001).
Pinilla, et al., "All-D Peptides Recognized by an Anti-carbohydrate Antibody Identified from a Positional Scanning Library," J. Mol. Biol., vol. 283, pp. 1013-1025 (1998).
Pircher, et al., "Lower receptor avidity required for thymic clonal deletion than for effector T-cell function," Nature vol. 351, pp. 482-485 (1991).
Platsoucas, et al. "Immune responses to human tumors: development of tumor vaccines." Anti Cancer Res. May-Jun. 2003; 23(3A): 1969-96. PMID: 12894571. Abstract Only.
Pogue, et al., "Amino-terminal alteration of the HLA-A*0201-restricted human immunodeficiency virus polypeptide increases complex stability and in vitro immunogenicity,"Proc. Natl. Acad. Sci. USA, vol. 97, pp. 8166-8170 (Aug. 1995).
Rock, et al. "Proteases in MHC Class I Presentation and Cross-Presentation," Journal of Immunology 2010; 184, pp. 9-15.
Salazar, et al., "Agonist Peptide From a Cytotoxic T-Lymphocyte Epitope of Human Carcinoembryonic Antigen Stimulates Production of TC1-Type Cytokines and Increases Tyrosince Phosphorylation More Efficiency Than Cognate Peptide," Int. J. Cancer, vol. 85, pp. 829-838 (2000).

Control PG5d Poly(I:C) PSWT PSVL

VARIABLE EPITOPE LIBRARY COMPOSITIONS AND METHODS OF THERAPEUTIC AND PROPHYLACTIC USE

CROSS-REFERENCE TO RELATED APPLICATIONS

The instant application is a continuation of U.S. application Ser. No. 14/991,807, filed Jan. 8, 2016, which claims the benefit of U.S. Provisional Patent Application No. 62/101,874, filed Jan. 9, 2015. These applications are incorporated herein by reference in their entirety for all purposes.

FIELD OF THE INVENTION

Embodiments of the present disclosure relate to compositions and methods for targeting antigenically variable pathogens and diseases. Certain embodiments disclosed herein relate to construction of variable epitope libraries (VELs) containing mutated versions of epitopes derived from antigens associated with various diseases of use for treating subjects in both therapeutic and prophylactic settings. Other embodiments provide compositions and methods for the production of VELs based on CTL-derived epitopes of survivin, an oncogenic inhibitor of apoptosis.

BACKGROUND OF THE INVENTION

The immune system protects a subject from possibly harmful substances by recognizing and responding to antigens. Antigens are substances, typically peptides, on the surface of cells, viruses, fungi, or bacteria. Nonliving substances such as toxins, chemicals, drugs, and foreign particles can also be antigens. The immune system recognizes and destroys substances that contain antigens. An epitope, also referred to as an antigenic determinant, is a portion of an antigen that is recognized by various molecules and cells that make up a subject's immune system (e.g., antibodies, T cells, B cells). An epitope is a specific peptide region of the antigen to which an antibody binds. T-cell epitopes, for example, are presented on the surface of antigen-presenting cells where they are typically bound to MHC molecules (major histocompatibility complex). An immune response is initiated following T cell recognition of antigen peptides in the context of self MHC molecules, and generally takes place in one of the host's secondary lymphoid compartments. Cellular activation is triggered by the binding of antigen to the T cell receptor (TCR), forming an antigen/TCR complex which transduces the antigen-specific extracellular stimulation across the plasma membrane, and generates intracellular signals which include the activation of protein kinase C and the increases in intracellular calcium. While signal transduction can lead to T cell unresponsiveness, positive signal transduction events trigger a series of additional biochemical processes that lead to an immune response in a subject.

One obstacle in the advancement for developing vaccines against pathogens with genetic variability is immune escape. Typically, immune escape involves amino acid substitutions in specific epitopes of a pathogenic antigen recognized by the host immune system (e.g., CTL, Th and B epitopes). Despite the degenerate nature of the interactions between a TCR of T cells and MHC/peptide complex on antigen-presenting cells, the majority of circulating variants are not recognized by CTLs. This may explain the immune system's failure in clearing or containing various pathogens. The ability of pathogens to escape immunity by mutating amino acids in epitopes or flanking regions (affecting the correct epitope processing) is an ongoing and dynamic process involving complex viral-host interactions. Other factors affecting the immune escape phenomenon include viral fitness, cost of mutations, immune pressure exerted by the host, host genetic factors, and viral load.

In the field of cancer epitope vaccines, the modified, optimized or variant peptides, also known as altered peptide ligands (APLs), mimotopes, heteroclitic peptides or peptide analogues, bearing mutated versions of natural epitopes derived from tumor-associated antigens (TAAs) are considered to be promising candidates for the development of vaccines. Comprehensive screening strategies, such as testing virtually every single amino acid substitution within an epitope by genetic screen, may lead to identification of superagonist APLs capable of eliciting potent anti-tumor patient-specific CTL responses when the native or wild type (WT) tumor-associated epitope fails. Central TCR-contact residues of antigenic peptides can be replaced even by non-peptidic units without loss of binding affinity to major histocompatibility complex (MHC) class-I molecules and T-cell triggering capacity. However, there are a very large number of potential epitopes expressed in tumors that are encoded by non-primary open reading frame (ORF) sequences (frame-shift mutations) or derived from other non-traditional sources, such as transcriptional/translational mechanisms or splicing events, collectively referred as epitopes derived from defective ribosomal products (DRiPs).

SUMMARY

Embodiments disclosed herein provide variable epitope library (VEL) vaccine compositions composed of one or more isolated peptides having amino acid sequences corresponding to an epitope of a pathogenic antigen, the one or more peptides spanning from about 7 to about 50 total amino acids, wherein from about 1% to about 50% of the total amino acids of the one or more peptides are variable amino acids, and wherein the composition generates an immune response when administered to a subject. Embodiments of the VEL vaccine composition also include a pharmaceutically acceptable excipient and/or adjuvant.

Embodiments disclosed herein also provide VELs comprising one or more synthetic isolated peptides having amino acid sequences corresponding to an epitope of a pathogenic antigen, the one or more peptides spanning from about 7 to about 50 total amino acids, wherein from about 1% to about 50% of the total amino acids of the one or more peptides are variable amino acids.

Other embodiments disclosed herein can provide for a VEL vaccine composition comprising one or more isolated polynucleotides encoding one or more peptides having amino acid sequences corresponding to an epitope of a pathogenic antigen, the one or more polynucleotides encoding one or more peptides spanning from about 7 to about 50 total amino acids, wherein the one or more polynucleotides have mutations that encode variable amino acids in from about 1% to about 50% of the total amino acids of the one or more peptides, and wherein the composition generates an immune response when administered to a subject. In accordance with these embodiments, the VEL vaccine compositions can further include a pharmaceutically acceptable excipient and/or adjuvant.

Embodiments disclosed herein can include a VEL comprising one or more isolated polynucleotides encoding one or more peptides having amino acid sequences corresponding to an epitope of a pathogenic antigen, the one or more polynucleotides encoding one or more peptides having from about 7 to about 50 total amino acids, further the one or more polynucleotides can contain one or more mutations that encode variable amino acids of about 1% to about 50% of the total amino acids of the one or more peptides.

VEL libraries and VEL vaccine compositions disclosed herein can include epitopes derived from pathogenic antigens of a survivin-derived CTL epitope. The VEL libraries and vaccine compositions can include variable amino acids that can be any of the 20 naturally occurring amino acids or derivatives thereof. The variable amino acids in the VEL libraries and vaccine compositions can be from about 10% to about 50% of the total amino acids of the one or more peptides, such that the complexity of the library or vaccine composition can be about 208 synthetic peptides.

Embodiments of the present disclosure provide for compositions and methods of producing VELs based on CTL-derived epitopes of survivin, an oncogenic inhibitor of apoptosis. VELs containing CTL-derived epitopes of survivin can be based for example, on the survivin-derived H-2Dd-restricted wild-type CTL epitope, GWEPDDNPI (SEQ ID NO: 2). In some embodiments, VELs containing CTL-derived epitopes of survivin can be based, for example, on the epitope GWXPXDXPI (SEQ ID NO: 1), where X is any one of the 20 naturally occurring amino acids or derivatives thereof.

VEL libraries and VEL vaccine compositions disclosed herein can be administered to a subject prophylactically or therapeutically to treat, prevent, and/or reduce the risk of developing various diseases from various pathogens, such as a cancerous tumor. Methods disclosed herein can include methods of treating cancer in a subject including injecting a variable epitope library vaccine composition having one or more isolated peptides with amino acid sequences corresponding to a survivin CTL epitope, the one or more peptides having from about 7 to about 50 total amino acids, wherein from about 1% to about 50% of the total amino acids of the one or more peptides are variable amino acids, and a pharmaceutically acceptable excipient and/or adjuvant. In accordance with these embodiments, when introduced to a subject, these compositions can generate an immune response. Methods disclosed herein include treating a subject diagnosed with cancer with one or more VEL compositions, where the cancer includes one or more tumors and the composition administered to the subject reduces the mass or volume of the one or more tumors.

In some embodiments, VEL libraries and VEL vaccine compositions disclosed herein can be produced by obtaining the amino acid sequence of one or more peptides corresponding to a survivin CTL epitope, and synthesizing the one or more peptides corresponding to a survivin CTL epitope, wherein the one or more peptides comprise from about 7 to about 50 total amino acids, and wherein from about 1% to about 50% of the total amino acids of the one or more peptides are variable amino acids. Embodiments can include combining the one or more peptides corresponding to a survivin CTL epitope into a mixture and adding at least one pharmaceutically acceptable excipient, agent and/or adjuvant to the mixture of one or more peptides corresponding to a survivin CTL epitope.

Unless otherwise defined, all technical and scientific terms used herein have the same meaning as commonly understood by one of ordinary skill in the art to which this disclosure belongs. Although methods and materials similar or equivalent to those described herein can be used to practice the subject matter of the disclosure, suitable methods and materials are described below. All publications, patent applications, patents, and other references mentioned herein are incorporated by reference in their entirety. In addition, the materials, methods, and examples are illustrative only and not intended to be limiting. Other features and advantages of the disclosure will be apparent from the following detailed description, and from the claims.

BRIEF DESCRIPTION OF THE DRAWINGS

The following drawings form part of the instant specification and are included to further demonstrate certain aspects of particular embodiments herein. The embodiments may be better understood by reference to one or more of these drawings in combination with the detailed description presented herein. This patent or application file contains at least one drawing executed in color. Copies of this patent or patent application publication with color drawing(s) will be provided by the Office upon request and payment of the necessary fee.

Figure 1A:
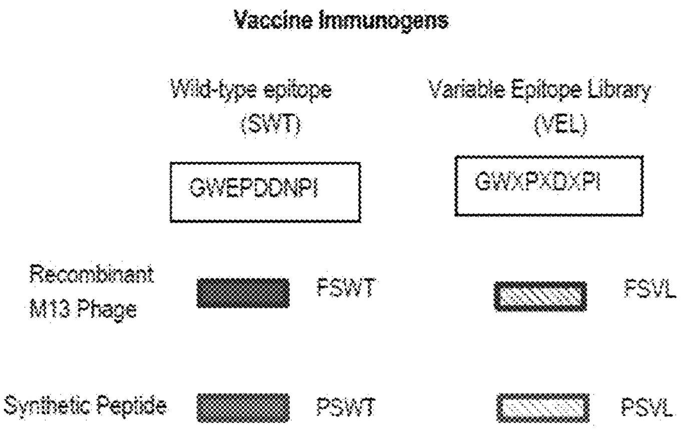
FIGS. 1A-1D are schematic diagrams illustrating the relative timing of tumor challenge, vaccination (prime and booster), and tumor isolation and analysis in experiments testing the efficacy of the phage display and synthetic peptide variable epitope libraries (VELs), according to one embodiment of the present disclosure.

While the disclosure is amenable to various modifications and alternative forms, specific embodiments have been shown by way of example in the drawings and are described in detail herein.

DETAILED DESCRIPTION

Embodiments of the present disclosure relate to compositions and methods for targeting antigenically variable pathogens and diseases. Certain embodiments disclosed herein relate to construction of variable epitope libraries (VELs) containing mutated versions of epitopes derived from antigens associated with various diseases of use for treating subjects in both therapeutic and prophylactic settings. Other embodiments provide compositions and methods for the production of VELs based on CTL-derived epitopes of survivin, an oncogenic inhibitor of apoptosis. Given this, and the dynamic and elusive nature of the tumor epitope landscape, there is a need to develop compositions and methods for targeting various antigenic epitopes to counteract immune escape and provide alternative treatments to these conditions.

Embodiments of the present disclosure provide for VEL compositions and methods of use for treatment of disease. In certain embodiments, a composition may include a synthetic peptide. In accordance with these embodiments, the synthetic peptide may include at least one epitope of a pathogen- or disease-specific polypeptide, where at least one amino acid residue of the peptide is substituted with each of the other nineteen common amino acid residues. In another embodiment, the present disclosure provides for VEL compositions that can include nucleic acid sequences or nucleic acid sequence derivatives. In accordance with this embodiment, the nucleic acid sequences or nucleic acid sequence derivatives may encode a peptide having at least one epitope of a pathogen- or disease-specific polypeptide, where at least one amino acid residue of the encoded peptide is substituted with each of the other nineteen common amino acid residues.

In one example, VEL compositions disclosed herein may be prepared by expression in a bacterial, viral, phage display, or eukaryotic expression system. In another example, the VEL compositions may be expressed and displayed on the surface of a recombinant bacteriophage, bacterium or yeast cell. In accordance with these embodiments, the composition of an epitope of a pathogen-specific nucleic acid or polypeptide disclosed herein may be selected from one or more epitopes of Human Immunodeficiency Virus (HIV), Simian Immunodeficiency Virus (SIV), Hepatitis A, Hepatitis B, Hepatitis C, rhinovirus, influenza virus, *Plasmodium falciparum*, tuberculosis, cancer (e.g., breast cancer), and infections salmon anemia virus (ISAV). Alternatively, the epitope of a disease-specific polypeptide may be one or more epitopes of a tumor associated antigen (TAA).

In another embodiment, a method for preparing and using a variable epitope library may include preparing the variable epitope library (VEL), injecting the library into a subject and inducing an immune response in the subject against the VEL. In accordance with this embodiment, preparing a VEL may include preparing a VEL bearing epitopes of a pathogen-specific polypeptide. In another embodiment, the method may include preparing a VEL where the VEL bears epitopes of a disease-specific polypeptide. In one example, inducing an immune response in a subject may include inducing an immune response effective to protect a subject against infection with a pathogen. In another example, inducing the immune response may include inducing the immune response effective to treat a subject infected with a pathogen or to protect the subject against onset of a condition such as cancer.

Variable Epitope Libraries (VELs)

Genetic variability of many pathogens and disease-related antigens can result in the selection of mutated epitope variants able to escape control by immune responses. This can be a major obstacle to vaccine development against certain pathogens. Embodiments herein relate to immunogens composed of variable epitope libraries derived from pathogens and disease-related antigens with genetic/antigenic variability in order to advance strategies for overcoming these issues with pathogenic organisms.

An immunogen vaccine composition that includes variable disease epitopes is referred to as a variable epitope library (VEL). VELs can be about 7 to about 50 amino acids (aa) or amino acid residues in length. For example, the polypeptides including a VEL can be $P_1P_2P_3 \ldots P_n$, where the numbers represent positions (P) of the various wild type amino acids, and where "n" represents the total polypeptide length and the position of the last amino acid. In various embodiments disclosed herein, at least one amino acid and as many as 90% of wild type amino acid residues can be randomly replaced by any of the 20 naturally occurring amino acid residues. As one of skill in the art would readily, VELs and VEL compositions are neither natural products nor naturally occurring, and VELs and VEL compositions are made-up of polypeptides that are neither natural products nor naturally occurring. Also, as one of skill in the art would readily recognize based, VELs and VEL compositions include polypeptides that are not yet known or identified, which enables VELs and VEL compositions to induce a broad range of protective immune responses when introduced to a subject before one or more mutated epitopes (before infection) emerges or when the amount of one or more mutated epitopes is low (early stages of infection and/or disease progression).

In alternative embodiments, VELs can contain nucleic acid sequence molecules comprising from about 20 to about 200 individual nucleotides that encode the variable epitope polypeptides. In other embodiments, VELs can contain one or more polypeptide molecules where from about 10% to about 50% of the total amino acids of the one or more polypeptide molecules are variable amino acids (replaced by any of the 20 naturally occurring amino acid residues or a derivative of a naturally occurring amino acid). In other embodiments, VELs can contain one or more polypeptides in which from about 20% to about 50% of the total amino acids of the one or more peptides are variable amino acids. In certain embodiments, VELs can contain one or more polypeptides in which from about 30% to about 50% of the total amino acids of the one or more peptides are variable amino acids. In yet other embodiments, VELs can contain one or more polypeptides in which from about 20% to about 40% of the total amino acids of the one or more peptides are variable amino acids.

For example, VELs and VEL vaccine compositions disclosed herein can be composed of a decapeptide, $P_1P_2P_3P_4P_5P_6P_7P_8P_9P_{10}$, that can be represented as $P_1X_2P_3X_4P_5X_6P_7X_8P_9X_{10}$ where X can be any of the 20 naturally occurring amino acids or derivatives of a naturally occurring amino acid, and where P can be an amino acid that is the same amino acid as that of the wild type epitope at that position. Similarly, another version of VEL based on the same decapeptide may be constructed by replacing wild type amino acid residues by X residues at odd positions and leaving this time wild type residues at even positions. While in these two particular decapeptide-based VELs each individual library member has 50% of wild type and 50% of random amino acid residues, this percentage or ratio (1:1) can be varied in such a manner that only one amino acid or up to 90% of a wild type amino acid sequence can be replaced by random amino acid residues.

The complexities of VELs can range from a VEL composed of 20 epitope variants where only one wild-type amino acid residue is replaced in the epitope by a random amino acid (e.g., 20 total peptides in the VEL), and up to about 208 epitope variants, where several amino acid residues are mutated. In some embodiments, the complexities of VELs can range from about 20 different amino acids to about 2010 different amino acids, depending on the number of variable amino acids, as one of skill in the art would recognize and understand based on the present disclosure and common knowledge. Further, the appearance of any amino acid other than wild type amino acid within the epitopes derived from genetically variable pathogens or disease-related antigens can include a pathogen, for example, including, but not limited to, Human Immunodeficiency Virus (HIV), Simian Immunodeficiency Virus (SIV), Hepatitis A, Hepatitis B, Hepatitis C, rhinovirus, influenza virus, *Plasmodium falciparum*, tuberculosis, cancer (e.g., breast cancer), and infections salmon anemia virus (ISAV), or some tumor antigens, where this event can be a frequent phenomenon. A VEL-based immunogen construction can represent antigenic diversity observed during the infection with the above mentioned pathogens and/or in diseases. Use of VEL immunogens as disclosed herein permits the generation of novel prophylactic and therapeutic vaccines capable of inducing a broad range of protective immune responses before the appearance of mutated epitopes (before infection) or when the amounts of mutated epitopes are low (early stages of infection and/or disease progression). VELs and VEL compositions can be used prophylactically and/or therapeutically to treat, prevent, and/or reduce the risk of developing various diseases from various pathogens, such as a cancerous tumor.

VELs can be generated based on defined pathogen or disease-related antigen-derived cytotoxic T lymphocyte (CTL), helper T lymphocyte (Th) or B lymphocyte epitopes and additionally, on epitopes derived from antigenically variable or relatively conserved regions of protein. Alternatively, VELs can be generated based on up to 50 amino acid long peptide regions of antigens containing clusters of epitopes. An individual VEL can contain: [1] variants of one CTL, Th or B cell epitope; [2] variants of several different CTL, Th or B cell epitopes; [3] any combination of these mutated CTL, Th and B cell epitopes expressed in a single up to 120 amino acid long artificial recombinant polypeptide; [4] up to 50 amino acid long mutated wild type-related peptide carrying several CTL, Th and/or B cell epitopes. Additionally, the VELs can be generated based on 7-50 amino acid peptides selected from antigenically variable or relatively conserved regions of pathogen- or disease-related proteins without a prior knowledge of the existence of epitopes in these peptide regions. Candidate epitopes can be selected from scientific literature or from public databases. It may be useful to include CTL epitopes in VELs, since the escape from protective CTL responses is an important mechanism for immune evasion by many pathogens, for example HIV and SIV.

VELs can take the form of DNA constructs, recombinant polypeptides or synthetic peptides and can be generated using standard molecular biology or peptide synthesis techniques, as discussed below. For example to generate a DNA fragment encoding particular epitope variants bearing peptides, a synthetic 40-70 nucleotide (nt) long oligonucleotide (oligo) carrying one or more random amino acid-coding degenerate nucleotide triplet(s) may be designed and produced. The epitope-coding region of this oligo (oligol) may contain non-randomized 9-15 nt segments at 5' and 3' flanking regions that may or may not encode natural epitope-flanking 3-5 amino acid residues. Then, 2 oligos that overlap at 5' and 3' flanking regions of oligol and carry nt sequences recognized by hypothetical restriction enzymes A and B, respectively, may be synthesized and after annealing reaction with oligol used in a PCR. This PCR amplification will result in mutated epitope library-encoding DNA fragments that after digestion with A and B restriction enzymes may be combined in a ligation reaction with corresponding bacterial, viral or eukaryotic cloning/expression vector DNA digested with the same enzymes. Ligation mixtures can be used to transform bacterial cells to generate the VEL and then expressed as a plasmid DNA construct, in a mammalian virus or as a recombinant polypeptide. This DNA can also be cloned in bacteriophage, bacterial or yeast display vectors, allowing the generation of recombinant microorganisms.

In a similar manner, DNA fragments bearing 20-200 individual nucleotides can encode various combinations of different mutated epitope variants. These nucleic acid molecules can be created using sets of long overlapping oligos and a pair of oligos carrying restriction enzyme recognition sites and overlapping with adjacent epitope-coding oligos at 5' and 3'flanking regions. These oligos can be combined, annealed and used in a PCR assembly and amplification reactions. The resulting DNAs may be similarly cloned in the above mentioned vectors.

In another embodiment, nucleic acid sequence molecules encoding mutated epitope clusters may also be obtained using pairs of wild type sequence-specific oligos carrying DNA restriction sites and pathogen- or antigen-derived genomic or cDNA as template in a PCR with an error-prone DNA polymerase. These DNAs also may be cloned in corresponding vectors. The VELs may be expressed in mammalian virus vectors, such as modified Vaccinia ankara, an adenoviral, a canary pox vectors, produced as recombinant polypeptides or as recombinant microorganisms and used individually as immunogens or may be combined and used as a mixture of VELs.

In one example, synthetic peptide VELs varying in length from 7 to 50 amino acid residues may be generated by solid phase Fmoc peptide synthesis technique where in a coupling step equimolar mixtures of all proteogeneic amino acid residues may be used to obtain randomized amino acid positions. This technique permits the introduction of one or more randomized sequence positions in selected epitope sequences and the generation of VELs with complexities of up to $10^9$.

Immunogens based on VELs can be useful for inducing protective immune responses against pathogens and tumors with antigenic variability, such as cancer, as well as may be effective in modulating allergy, inflammatory and autoimmune diseases. In one embodiment, vaccine compositions containing one or more VELs may be formulated with a pharmaceutically acceptable carrier, excipient and/or adjuvant, and administered to a subject, such as a non-human animal or a human patient. Compositions containing VELs comprising peptides can be administered to a subject, such as a human, therapeutically or prophylactically at dosages ranging from about 100 m to about 1 mg of isolated peptides. Compositions containing VELs including nucleic acid sequences can be administered to a subject, such as a human, therapeutically or prophylactically at dosages ranging from about $1\times10^{10}$ to about $5\times10^{15}$ CFU of bacteriophage particles. In some embodiments, VELs administered to a human subject can reduce onset of a disease such as a cancer (e.g., a malignant cancer such as a malignant tumor involving survivin) and/or VELs administered to a human subject can treat a disease already existing in the human subject (e.g., a cancerous malignancy involving survivin). Other approaches for the construction of VELs, expression and/or display vectors, optimum vaccine composition, routes for vaccine delivery and dosing regimens capable of inducing prophylactic and therapeutic benefits may be determined by one skilled in the art based on the present disclosure. For example, compositions containing VELs can be administered to a subject as a single dose application, as well as a multiple dose (e.g., booster) application. Multiple dose applications can include, for example, administering from about 1 to about 25 total dose applications, with each dose application administered at one or more dosing intervals that can range from about 7 days to about 14 days (e.g., weekly). In some embodiments, dosing intervals can be administered daily, two times daily, twice weekly, weekly, monthly, bi-monthly, annually, or bi-annually, depending on the particular needs of the subject and the characteristics of the condition being treated or prevented (or reducing the risk of getting the condition), as would be appreciated by one of skill in the art based on the present disclosure.

The skilled artisan will realize that in alternative embodiments, less than the 20 naturally occurring amino acids may be used in a randomization process. For example, certain residues that are known to be disruptive to protein or peptide secondary structure, such as proline residues, may be less preferred for the randomization process. VELs may be generated with the 20 naturally occurring amino acid residues or with some subset or derivatives of the 20 naturally occurring amino acid residues. In various embodiments, in addition to or in place of the 20 naturally occurring amino acid residues, the VELs may contain at least one modified amino acid, including but not limited to, those presented on Table 1 below.

TABLE 1

Modified amino acid residues

| Abbr. | Amino Acid |
|---|---|
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

VELs may be made by any technique known to those of skill in the art, including the expression of polypeptides or peptides through standard molecular biological techniques or the chemical synthesis of peptides. The nucleotide and polypeptide and peptide sequences corresponding to various pathogen- or disease-related antigens are known in the art and may be found at computerized databases known to those of ordinary skill in the art. One such database is the National Center for Biotechnology Information's Genbank and GenPept databases. Any such known antigenic sequence may be used in the practice of the claimed methods and compositions.

Combinatorial Libraries

Combinatorial libraries of such compounds or of such targets can be categorized into three main categories. The first category relates to the matrix or platform on which the library is displayed and/or constructed. For example, combinatorial libraries can be provided (i) on a surface of a chemical solid support, such as microparticles, beads or a flat platform; (ii) displayed by a biological source (e.g., bacteria or phage); and (iii) contained within a solution. In addition, three dimensional structures of various computer generated combinatorial molecules can be screened via computational methods.

Combinatorial libraries can be further categorized according to the type of molecules represented in the library, which can include, (i) small chemical molecules; (ii) nucleic acids (DNA, RNA, etc.); (iii) peptides or proteins; and (iv) carbohydrates.

The third category of combinatorial libraries relates to the method by which the compounds or targets are synthesized, such synthesis is typically effected by: (i) in situ chemical synthesis; (ii) in vivo synthesis via molecular cloning; (iii) in vitro biosynthesis by purified enzymes or extracts from microorganisms; and (iv) in silico by dedicated computer algorithms.

Combinatorial libraries indicated by any of the above synthesis methods can be further characterized by: (i) split or parallel modes of synthesis; (ii) molecules size and complexity; (iii) technology of screening; and (iv) rank of automation in preparation/screening.

The complexity of molecules in a combinatorial library depends upon the diversity of the primary building blocks and possible combinations thereof. Furthermore, several additional parameters can also determine the complexity of a combinatorial library. These parameters include (i) the molecular size of the final synthesis product (e.g., oligomer or small chemical molecule); (ii) the number of bonds that are created in each synthesis step (e.g., one bond vs. several specific bonds at a time); (iii) the number of distinct synthesis steps employed; and (iv) the structural complexity of the final product (e.g., linear vs. branched molecules).

Combinatorial libraries can be synthesized of several types of primary molecules, including, but not limited to, nucleic and amino acids and carbohydrates. Due to their inherent single bond type complexity, synthesizing nucleic and amino acid combinatorial libraries typically necessitates only one type of synthesis reaction. On the other hand, due to their inherent bond type complexity, synthesizing complex carbohydrate combinatorial libraries necessitates a plurality of distinct synthesis reactions.

Expression of Proteins or Peptides

In certain embodiments, it may be preferred to make and use an expression vector that encodes and expresses a particular VEL. Gene sequences encoding various polypeptides or peptides may be obtained from GenBank and other standard sources, as disclosed above. Expression vectors containing genes encoding a variety of known proteins may be obtained from standard sources, such as the American Type Culture Collection (Manassas, Va.). For relatively short VELs, it is within the skill in the art to design synthetic DNA sequences encoding a specified amino acid sequence, using a standard codon table, as discussed above. Genes may be optimized for expression in a particular species of host cell by utilizing well-known codon frequency tables for the desired species. Genes may represent genomic DNA sequences, containing both introns and exons, or more preferably comprise cDNA sequences, without introns.

Regardless of the source, a coding DNA sequence of interest can be inserted into an appropriate expression system. The DNA can be expressed in any number of different recombinant DNA expression systems to generate large amounts of the polypeptide product, which can then be purified and used in various embodiments of the present disclosure.

Examples of expression systems known to the skilled practitioner in the art include bacteria such as *E. coli*, yeast such as Pichia pastoris, baculovirus, and mammalian expression systems such as in Cos or CHO cells. Expression is not limited to single cells, but may also include protein production in genetically engineered transgenic animals, such as rats, cows or goats. A complete gene can be expressed or, alternatively, fragments of the gene encoding portions of polypeptide can be produced.

In certain broad applications of the disclosure, the sequence encoding the polypeptide may be analyzed to detect putative transmembrane sequences. Such sequences are typically very hydrophobic and are readily detected by the use of standard sequence analysis software, such as MacVector (IBI, New Haven, Conn.). The presence of transmembrane sequences may be deleterious when a recombinant protein is synthesized in many expression systems, especially *E. coli*, as it leads to the production of insoluble aggregates which are difficult to renature into the native conformation of the protein. Deletion of transmembrane sequences typically does not significantly alter the conformation of the remaining protein structure. Deletion of transmembrane-encoding sequences from the genes used for expression can be achieved by standard techniques. For example, fortuitously-placed restriction enzyme sites can be used to excise the desired gene fragment, or PCR-type amplification can be used to amplify only the desired part of the gene.

The gene or gene fragment encoding a polypeptide may be inserted into an expression vector by standard subcloning techniques. An *E. coli* expression vector may be used which produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6× His system (Qiagen, Chatsworth, Calif.).

Some of these systems produce recombinant polypeptides bearing only a small number of additional amino acids, which are unlikely to affect the activity or binding properties of the recombinant polypeptide. For example, both the FLAG system and the 6× His system add only short sequences, both of which have no adverse effect on folding of the polypeptide to its native conformation. Other fusion systems are designed to produce fusions wherein the fusion partner is easily excised from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The expression system used may also be one driven by the baculovirus polyhedron promoter. The gene encoding the polypeptide may be manipulated by standard techniques in order to facilitate cloning into the baculovirus vector. One baculovirus vector is the pBlueBac vector (Invitrogen, Sorrento, Calif.). The vector carrying the gene for the polypeptide is transfected into Spodoptera frugiperda (Sf9) cells by standard protocols, and the cells are cultured and processed to produce the recombinant protein.

To express a recombinant encoded protein or peptide, whether mutant or wild-type, one would prepare an expression vector that comprises one of the isolated nucleic acids under the control of, or operatively linked to, one or more promoters. To bring a coding sequence "under the control of" a promoter, one positions the 5' end of the transcription initiation site of the transcriptional reading frame generally from about 1 to about 50 nucleotides "downstream" (3') of the chosen promoter. The "upstream" promoter stimulates transcription of the DNA and promotes expression of the encoded recombinant protein.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which may be used by the microbial organism for expression of its own proteins.

In addition, phage vectors containing replicon and control sequences that are compatible with the host microorganism may be used as transforming vectors in connection with these hosts. For example, the phage lambda GEMTM-11 may be utilized in making a recombinant phage vector which may be used to transform host cells, such as *E. coli* LE392.

Further useful vectors include pIN vectors and pGEX vectors, for use in generating glutathione S transferase (GST) soluble fusion proteins for later purification and separation or cleavage. Other suitable fusion proteins are those with B galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, Autographa californica nuclear polyhedrosis virus (AcNPV) is used as a vector to express foreign genes. The virus grows in Spodoptera frugiperda cells. The isolated nucleic acid coding sequences are cloned into non-essential regions (e.g., polyhedrin gene) of the virus and placed under control of an AcNPV promoter (e.g., polyhedrin promoter). Successful insertion of the coding sequences results in the inactivation of the polyhedrin gene and production of non-occluded recombinant virus (e.g., virus lacking the proteinaceous coat coded for by the polyhedrin gene). These recombinant viruses are then used to infect Spodoptera frugiperda cells in which the inserted gene is expressed.

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cells lines or host systems may be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter) as known in the art.

A number of viral based expression systems may be utilized, for example, commonly used promoters are derived from polyoma, Adenovirus 2, and most frequently Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication.

In one example where an adenovirus is used as an expression vector, the coding sequences may be ligated to an adenovirus transcription/translation control complex (e.g., the late promoter and tripartite leader sequence). This chimeric gene may then be inserted in the adenovirus genome by in vitro or in vivo recombination. Insertion in a non-essential region of the viral genome (e.g., region E1 or E3)

will result in a recombinant virus that is viable and capable of expressing proteins in infected hosts.

Specific initiation signals known in the art may also be required for efficient translation of the claimed isolated nucleic acid coding sequences. One of ordinary skill in the art would readily be capable of determining this and providing the necessary signals.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination. For long-term, high-yield production of recombinant proteins by stable expression known in the art may be required.

A number of selection systems may be used, including but not limited to, the herpes simplex virus thymidine kinase, hypoxanthine-guanine phosphoribosyltransferase and adenine phosphoribosyltransferase genes, in tk-, hgprt- or aprt-cells, respectively. Also, antimetabolite resistance may be used as the basis of selection for dhfr, that confers resistance to methotrexate; gpt, that confers resistance to mycophenolic acid; neo, that confers resistance to the aminoglycoside G-418; and hygro, that confers resistance to hygromycin. These and other selection genes may be obtained in vectors from, for example, ATCC or may be purchased from a number of commercial sources known in the art (e.g., Stratagene, La Jolla, Calif.; Promega, Madison, Wis.).

Where substitutions into naturally occurring pathogen- or disease-related polypeptide sequences are desired, the nucleic acid sequences encoding the native polypeptide sequence may be manipulated by well-known techniques, such as site-directed mutagenesis or by chemical synthesis of short oligonucleotides followed by restriction endonuclease digestion and insertion into a vector, by PCR based incorporation methods, or any similar method known in the art.

Protein Purification

In certain embodiments a polypeptide or peptide may be isolated or purified. Protein purification techniques are well known to those of skill in the art. These techniques involve, at one level, the homogenization and crude fractionation of the cells, tissue or organ to polypeptide and non-polypeptide fractions. The peptide or polypeptide of interest may be further purified using chromatographic and electrophoretic techniques to achieve partial or complete purification (or purification to homogeneity). Analytical methods well suited to the preparation of a pure peptide are ion-exchange chromatography, gel exclusion chromatography, polyacrylamide gel electrophoresis, affinity chromatography, immunoaffinity chromatography and isoelectric focusing. An efficient method of purifying peptides is fast performance liquid chromatography (FPLC) or even HPLC.

A purified polypeptide or peptide is intended to refer to a composition, isolatable from other components, wherein the polypeptide or peptide is purified to any degree relative to its naturally-obtainable state. An isolated or purified polypeptide or peptide, therefore, also refers to a polypeptide or peptide free from the environment in which it may naturally occur. Generally, "purified" will refer to a polypeptide or peptide composition that has been subjected to fractionation to remove various other components. Where the term "substantially purified" is used, this designation will refer to a composition in which the polypeptide or peptide forms the major component of the composition, such as constituting about 50%, about 60%, about 70%, about 80%, about 90%, about 95%, or more of the polypeptides in the composition. Various methods for quantifying the degree of purification of the polypeptide or peptide are known to those of skill in the art in light of the present disclosure. These include, for example, assessing the amount of polypeptides within a fraction by SDS/PAGE analysis.

Various techniques suitable for use in protein purification are contemplated herein and are well known. There is no general requirement that the polypeptide or peptide always be provided in their most purified state. Indeed, it is contemplated that less substantially purified products will have utility in certain embodiments. In another embodiment, affinity chromatography may be required and any means known in the art is contemplated herein.

Formulations and Routes for Administration to Subjects

Where clinical applications are contemplated, it will be necessary to prepare pharmaceutical compositions (e.g., VEL vaccine compositions) in a form appropriate for the intended application. Generally, this will entail preparing compositions that are essentially free of impurities that could be harmful to human or animal subjects.

One generally will desire to employ appropriate salts and buffers to render polypeptides stable and allow for uptake by target cells. Aqueous compositions may comprise an effective amount of polypeptide dissolved or dispersed in a pharmaceutically acceptable carrier or aqueous medium. Such compositions also are referred to as innocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the polypeptides of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. This includes oral, nasal, buccal, rectal, vaginal or topical. Alternatively, administration may be by orthotropic, intradermal, subcutaneous, intramuscular, intraperitoneal, intraarterial or intravenous injection. Such compositions normally would be administered as pharmaceutically acceptable compositions, as described above.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In certain examples, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. Regarding sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The VELs and VEL compositions of the present disclosure may also be used in conjunction with targeted therapies, including but not limited to, therapies designed to target tumors and the cells underlying the tumor. Many different targeted therapies have been approved for use in cancer treatment. For example, these therapies can include hormone therapies, signal transduction inhibitors, gene expression modulator, apoptosis inducer, angiogenesis inhibitor, immunotherapies, and toxin delivery molecules. Additionally, cancer vaccines and gene therapy can be considered targeted therapies because they interfere with the growth of specific cancer cells (e.g., breast cancer cells).

EXAMPLES

Embodiments of the present disclosure are included to demonstrate certain embodiments presented herein. It should be appreciated by those of skill in the art that the techniques disclosed in the examples that follow represent techniques discovered to function well in the practices disclosed herein. However, those of skill in the art should, in light of the present disclosure, appreciate that many changes can be made in the certain embodiments which are disclosed and still obtain a like or similar result without departing from the spirit and scope herein.

Example 1

Construction of Variable Epitope Libraries (VELs)

In order to avoid tumor escape, it is desirable to target a tumor antigen that is essential for tumor survival and expressed by tumors at high levels. One of these antigens is survivin, an oncogenic inhibitor-of-apoptosis protein, which is expressed at high levels in virtually all malignancies and is commonly referred to as a universal tumor antigen. Additionally, survivin-specific T-cell reactivity strongly correlates with tumor response and subject survival. In one embodiment of the present disclosure, phage display VELs and synthetic peptide VELs were generated based on the survivin-derived CTL epitope presented below:

GWXPXDXPI (SEQ ID NO: 1), where X is any of the 20 naturally occurring amino acids or derivatives thereof.

VELs were generated using the recombinant M13 phage display system based on the survivin-derived H-2Dd-restricted wild-type CTL epitope, GWEPDDNPI (SEQ ID NO: 2), referred to as SWT. The recombinant phage display library comprising the wild-type survivin epitope is referred to as FSWT, and the recombinant phage display VEL comprising the variable epitopes of wild-type survivin is referred to as FSVL (FIG. 1A). Additionally, the synthetic peptide library comprising the wild-type survivin epitope is referred to as PSWT, and the synthetic peptide VEL comprising the variable epitopes of wild-type survivin is referred to as PSVL (FIG. 1A). The epitope variants comprising the combinatorial VELs, were generated using degenerate oligonucleotides encoding a library of epitope variants with structural composition GWXPXDXPI, (SEQ ID NO: 1), where X is any of 20 natural amino acids (SEQ ID NO: 1). The DNA fragments corresponding to the SWT and SVL, respectively, were amplified by PCR and cloned into pG8SAET phagemid vector that allows the expression of epitopes at high copy numbers as peptides fused to phage cpVIII. The amino acids at the MHC-binding anchor positions were maintained within the epitope, while mutations were introduced at positions responsible for interaction with TCR. Thus, each variant epitope has random amino acid substitutions (mutations) at 3 defined positions within the SWT and, the theoretical complexity of such library is 8×103 individual members. The FSVL phage library has a complexity of 10,500 original clones.

As described above, VELs can also be generated based on other epitopes found within the full length survivin peptide. For example, VELs can be generated based on the epitope presented below:

```
                                      (SEQ ID NO: 3)
AGFIHCPTENEPDLAQXFFXFKELEGWXPXDXPIEEHXKHSXGCAFLX
```

where X is any one of the 20 naturally occurring amino acids or derivatives thereof.

The various sequences for the libraries described above were verified and a subset was generated to T-cell assays and a panel of epitopes for in vivo studies. Twenty-six phage clones were randomly isolated from the FSVL, and the amino acid sequences of the corresponding peptides/epitopes were determined after DNA sequencing. As presented in Table 2, 12-16 different amino acids were detected at each respective variable amino acid position in the 26 epitope variants, indicating an acceptable level of epitope diversity. In order to generate a panel of variant epitopes for in vivo studies, 87 phage clones were randomly isolated from the FSVL epitope library, and used in T-cell assays. Also, a non-related phage clone FB22 was used as the control in immunization experiments.

Example 2

Anti-Tumor Effects in Mice Vaccinated with VELs

Figure 1B:
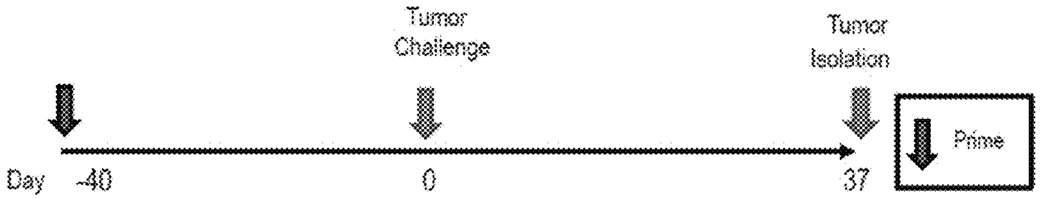

An analysis of the immunogenic properties of VEL-based vaccine compositions before (e.g., prophylactic treatment) and after (e.g., therapeutic treatment) tumor challenge was performed. BALB/c mice were challenged by exposure to syngeneic 4T1 tumor cell. Groups of mice were immunized with FSVL, FSWT or FB22 control phages expressing VEL-based epitope variants, wild-type SWT epitopes, or the control non-related B22 epitopes, respectively, by intravenous (iv) injection as illustrated schematically in FIG. 1. As a control, a group of non-immunized mice was included. Forty days after vaccination, all mice were inoculated with 104 4T1 tumor cells and monitored prospectively for development of tumors (FIG. 1B). As demonstrated in FIG. 2A, a statistically significant ($P<0.05$) tumor growth inhibition in a prophylactic setting was observed in FSVL-vaccinated mice compared with FSWT-vaccinated mice, and controls (e.g., FB22-vaccinated mice and control non-immunized mice receiving only a 4T1 cell transplant).

To test the anti-tumor effects of VELs on already established tumors, a mouse model was used. Mice were transplanted with 4T1 cells and vaccinated with FSVL, FSWT and FB22 phages, or PSWT (synthetic peptide corresponding to SWT epitope GWEPDDNPI) (SEQ ID NO: 2), PSVL (synthetic peptides corresponding to the SVL (GWXPXDXPI) (SEQ ID NO: 1), peptide/epitope library) and PG5D (a control peptide/epitope library (A[G/F] PXXXXX[L/M]), by single i.v. and s.c. injection (FIG. 2B and FIG. 2D, respectively), on day 5 after tumor challenge, as illustrated schematically in FIG. 1C. Inhibition of tumor growth was demonstrated in FSVL-vaccinated mice (FIG. 2B, single injection) and in PSVL-vaccinated mice (FIG. 2D, single injection), as compared to mice immunized with FSWT, PSWT, or non-immunized tumor-bearing mice.

Figure 1C:
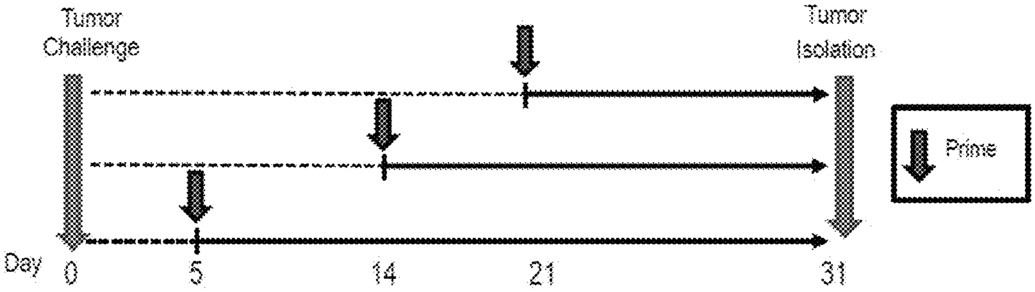
Figure 1D:
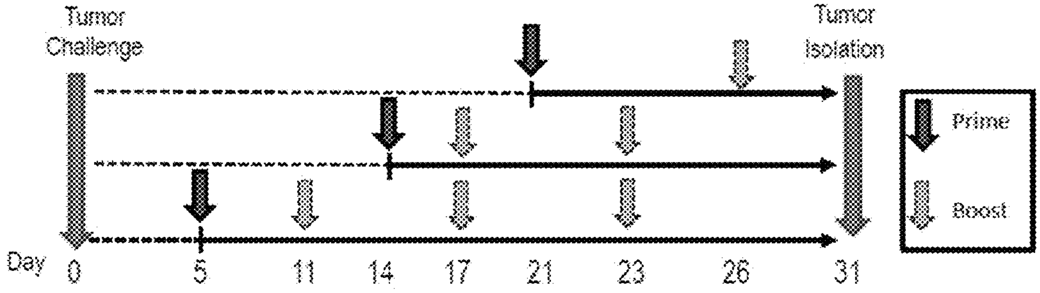
Figure 2A:
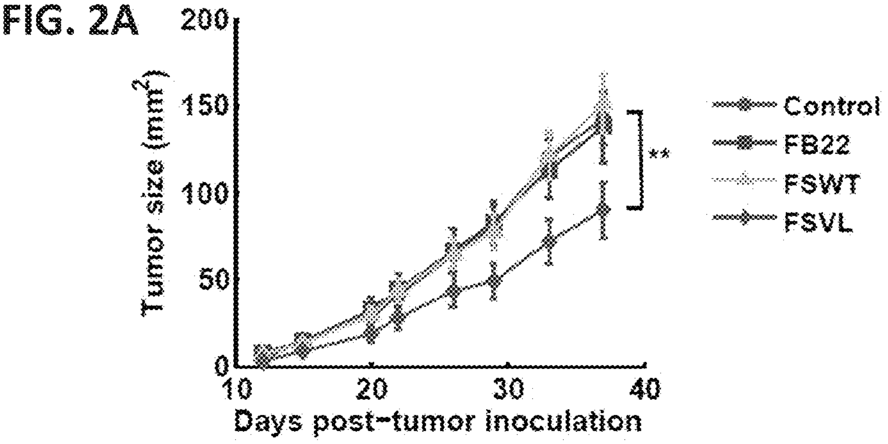
FIG. 2A is a graphical representation of the efficacy of prophylactic administration of a phage display VEL based on a survivin-derived CTL epitope for reducing 4T1-induced tumor growth, according to one embodiment of the present disclosure.
Figure 2B:
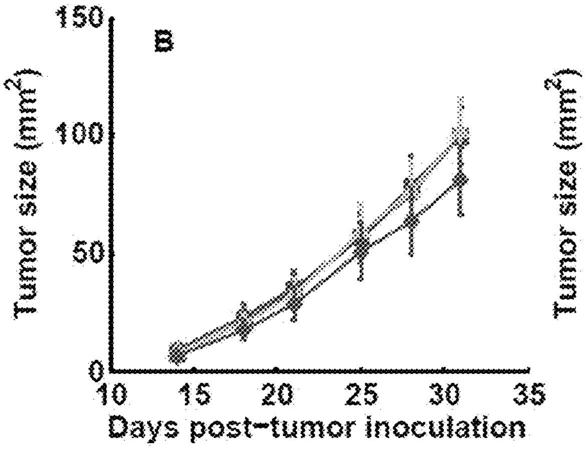
FIG. 2B is a graphical representation of the efficacy of therapeutic administration (single injection) of a phage display VEL based on a survivin-derived CTL epitope for reducing 4T1-induced tumor growth, according to embodiments herein.
Figure 2C:
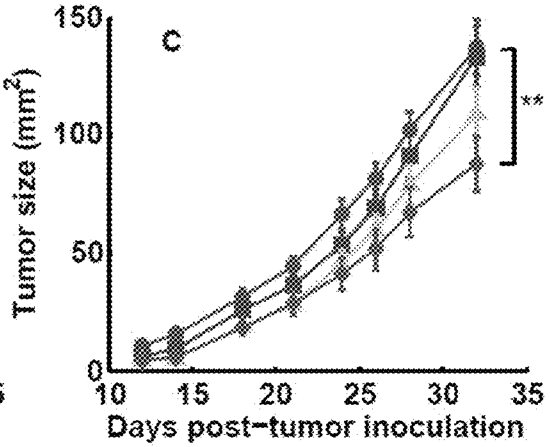
FIG. 2C is a graphical representation of efficacy of therapeutic administration (multiple injections) of a phage display VEL based on a survivin-derived CTL epitope for reducing 4T1-induced tumor growth, according to embodiments herein.
Figure 2D:
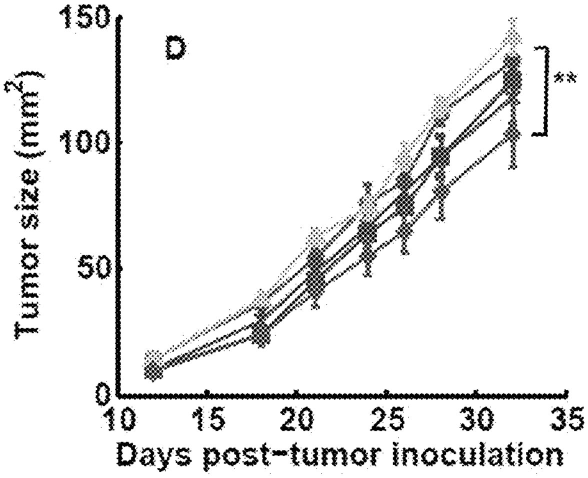
FIG. 2D is a graphical representation of efficacy of therapeutic administration (single injection) of a synthetic peptide VEL based on a survivin-derived CTL epitope for reducing 4T1-induced tumor growth, according to embodiments herein.
Figure 2E:
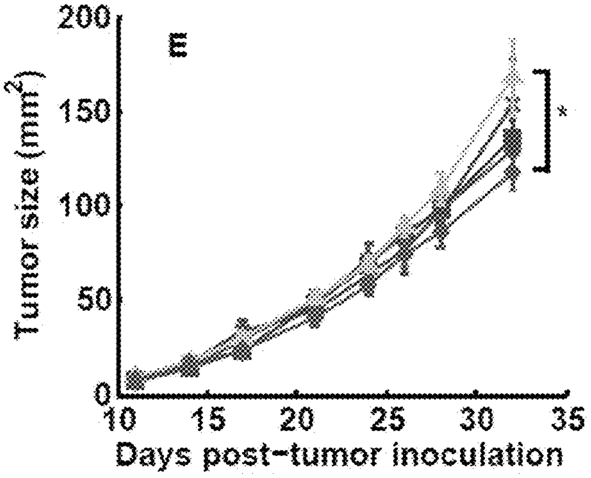
FIG. 2E is a graphical representation of efficacy of therapeutic administration (multiple injections) of a synthetic peptide VEL based on a survivin-derived CTL epitope for reducing 4T1-induced tumor growth, according to embodiments herein.

Single vaccinations of mice with phage and synthetic peptide VELs on days 14 and 21 after tumor inoculation was not inhibitory for tumor growth (FIG. 1C). However, multiple immunizations (e.g., boosters) enhanced anti-tumor effects. As illustrated in FIG. 2C, three booster immunizations with FSVL improved the vaccine potency as compared with a single priming dose of FSVL (FIG. 2B), resulting in statistically significant tumor growth inhibition. However, three booster immunizations of mice according to the same schedule with synthetic peptide VELs did not lead to as significant of an increase in vaccine efficacy (FIG. 2E) as compared to a single priming dose (FIG. 2D). No significant anti-tumor effect was observed in mice bearing established (>10 mm2, day 14) or large (>40 mm2, day 21) tumors that were primed on days 14 or 21, and then received one or two booster immunizations on days 17 and 23 or on day 26, respectively, by phage or synthetic peptides (FIG. 1D). The immunized mice undergoing necropsy were also routinely assessed for evidence of autoimmunity; no abnormal lymphocytic infiltrates into organs were observed.

These data indicate that vaccination with VELs in the form of recombinant M13 phage particles and synthetic peptides has statistically significant anti-tumor effects when applied prophylactically (FIG. 2A) and therapeutically (FIGS. 2B-2E) in a mouse 4T1 mammary carcinoma model.

Example 3

Cellular Immune Responses Induced by VELs

Immunization with FSVL phage-displayed VELs were able to elicit immune responses to CTL epitope variants as indicated with T-cell proliferation assays. Mice were immunized by a single injection with FSVL or FSWT, and a subset of these mice were challenged with 4T1 cells 40 days later, while the rest of the mice were not challenged with tumor cells. Fifteen days post-challenge, splenocytes were prepared from both groups, stimulated in vitro using the panel of 87 phage clones, and the breadth (e.g., number of responding epitope variants) and the magnitude of total T-cell proliferative responses were measured by flow cytometry. To more clearly visualize differential recognition of epitope variants by the spleen cells of mice immunized with FSVL or FSWT, differences observed between experimental groups were calculated, and illustrated in FIGS. 3A-3D.

Figure 3A:
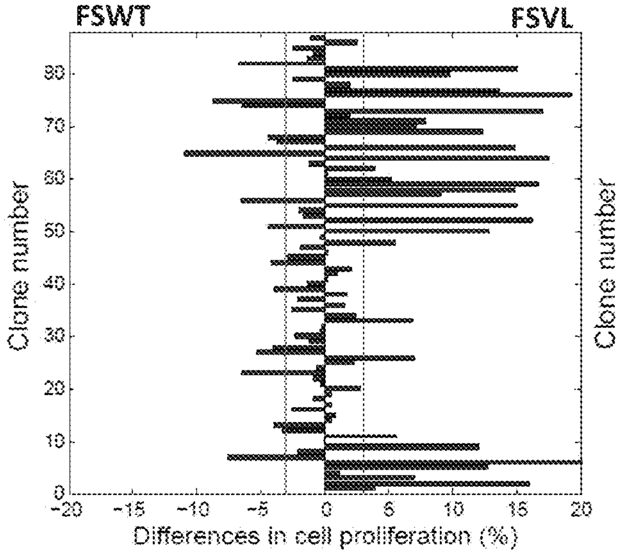
FIG. 3A is a graphical representation of the efficacy of a phage display VEL based on a survivin-derived CTL epitope to induce a cellular immune response in immunized mice (FSVL or FSWT) after 4T1-induced tumor challenge, according to embodiments herein.

Immunization with the FSVL library generated a pool of splenocytes with highly variable capacities to recognize individual epitope variants (see, e.g., FIG. 3A). The levels of proliferation of the splenocytes from mice immunized with FSVL and FSWT were from about 8.50-43.60% to about 9.61-28.41%, respectively ($p<0.006$) (FIG. 3A). Additionally, 29 out of 87 epitope variants (or 33%) showed higher stimulatory capacity against cells from FSVL-immunized mice compared with FSWT-immunized mice (3-20% increase in percentages of cell proliferation). Only 14 epitope variants showed about a 3-11% increase in stimulatory capacity against cells from FSWT-immunized mice (FIG. 3A; 29/87 as compared to 14/87; $p<0.009$). These data indicate the superior immunogenicity of FSVL over FSWT and the induction of long-lasting immune memory. Additionally, 18 epitope variants were more immunogentic than the wild-type epitope-expressing FSWT phage. The FSWT phage elicited a more than two-fold stronger immunogenic response against splenocytes from both the FSVL- and FSWT-immunized mice as compared to the FB22 control phage. The FB22 control phage produced only background levels of cell proliferation (data not shown).

Figure 3B:
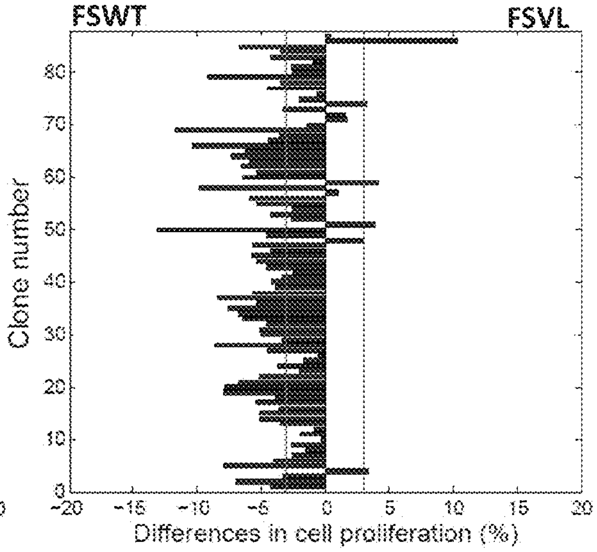
FIG. 3B is a graphical representation of the efficacy of prophylactic administration (single injection) of a phage display VEL based on a survivin-derived CTL epitope for inducing a cellular immune response after 4T1-induced tumor challenge, according to embodiments herein.

After tumor challenge (e.g., therapeutic treatment), however, a strong inhibition of these immune responses was observed (FIG. 3B). Epitope variants were able to stimulate cells from mice immunized with FSWT more efficiently than cells from FSVL-immunized mice (59/87 as compared to 3/87 p<0.0001). After tumor challenge, both FSWT and FB22 controls induced similar background level of cell proliferation against spleen cells from either FSVL- or FSWT-immunized mice (data not shown). The observed pattern of epitope recognition was changed after tumor challenge leading to general inhibition of cell proliferation and to preferential recognition by variant epitopes of spleen cells from FSWT-immunized mice compared with FSVL-immunized animals (FIG. 3B).

Figure 3C:
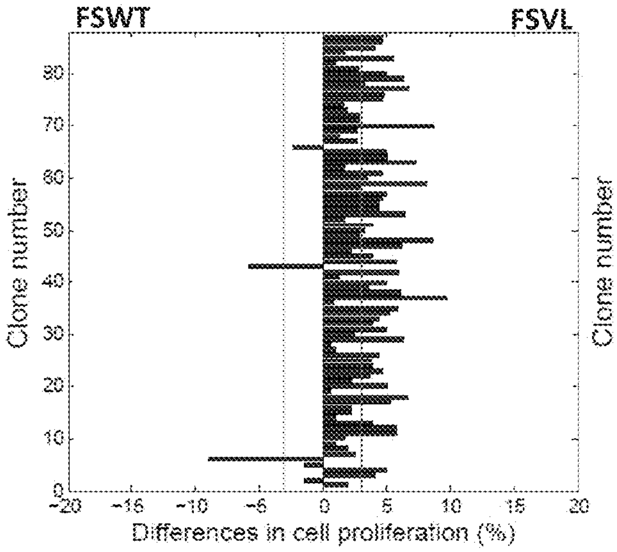
FIG. 3C is a graphical representation of the efficacy of therapeutic administration (single injection) of a phage display VEL based on a survivin-derived CTL epitope for inducing a cellular immune response, according to embodiments herein.

The ability of the FSVL phage-display VEL to elicit immune responses to CTL epitope variants in therapeutic setting was also tested. Groups of mice were immunized by a single injection with FSVL, FSWT or the control FB22 phage on day 5 after tumor challenge, and a subset of mice were left naïve to any treatment (FIG. 3C). Fifteen days after the tumor challenge, splenocytes were prepared, stimulated in vitro with the panel of 87 phage clones, and analyzed using the T-cell proliferation assay. As illustrated in FIG. 3C, the general levels of proliferation of cells from FSVL- and FSWT-immunized mice was lower (with absolute values of from about 6.86-28.46% to about 12.14-27.64%, respectively; p<0.0001) than those obtained in prophylactic study (FIG. 3B). Cells from FSVL-immunized mice exhibited proliferative responses to 53 epitope variants (about 61% of variants) with values from about 3-10% above those obtained with cells from FSWT-immunized mice (53/87 as compared to 2/87; p<0.0001). The spleen cells from tumor-bearing mice immunized with the control FB22 phage demonstrated only background levels of cell proliferation against almost all variant epitopes (data not shown) indicating the induction of epitope variant- and epitope-specific immune responses by the VEL-bearing FSVL. In the presence of an established tumor in an acceptable mouse model, vaccination with FSVL produced superior immunogenicity compared to vaccination with FSWT. The responses against individual epitope variants were highly reproducible and from about 11 to about 18 epitope variants resulted in a stronger immune response than the FSWT wild-type epitope against cells from FSVL- and FSWT-immunized mice, respectively (data not shown). These data indicate that in both prophylactic and therapeutic settings, several epitope variants are more potent immunogens than the wild-type CTL epitope.

Figure 3D:
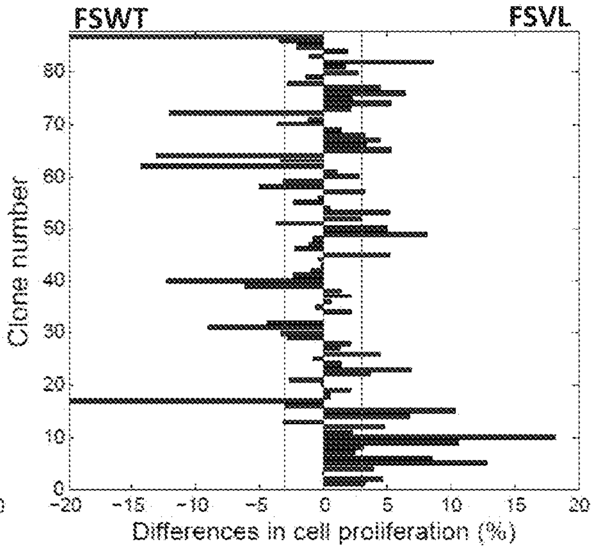
FIG. 3D is a graphical representation of the efficacy of a phage display VEL based on a survivin-derived CTL epitope to induce a cellular immune response in non-immunized mice after 4T1-induced tumor challenge, according to embodiments herein.

The antigenic properties of the generated panel of epitope variants against spleen cells obtained from non-immunized control mice was also tested in order to measure a background level of immune recognition and to determine the changes induced in epitope reactivity profile after tumor challenge. While the general level of proliferation of splenocytes from both groups of mice were similar (from about 10.49-37.79% to about 11.73-37.73%, respectively; p<0.309), the spontaneous cell-stimulating capacities of 27 epitope variants (or 31%) were diminished after tumor challenge, as indicated by decreased percentages of cell proliferation (differences between groups were about 3-18%), as illustrated in FIG. 3D. Additionally, 17 epitope variants (or 19%) were preferentially activating splenocytes from tumor-bearing mice as compared with control mice (about 3-21% of differences; 27/87 as compared to 17/87; p<0.083). Again, as in the example of tumor challenge of immunized mice described above, neither FSWT nor the FB22 controls stimulated splenocyte proliferation from naïve or tumor-inoculated mice.

Together, these data demonstrate that vaccination with VELs based on a survivin-derived CTL epitope induces specific anti-tumor cellular immune responses and suggest the superiority of VEL-based immunogens over immunogens carrying defined wild-type epitope in their capacity to induce broad and potent immune responses without inducing harmful autoimmune reactions.

Example 4

Phenotypic Analysis of Activated Lymphocytes

Flow cytometry and intracellular cytokine staining (ICS) assays were performed to determine which subpopulations of T-cells were proliferating in the T-cell proliferation assays, and to test whether immunization with VELs induces epitope-specific activation of both CD4+IFN-γ+ and CD8+ IFN-γ+ cells (FIGS. 4A-4D). Pooled splenocytes from each group of mice used in prophylactic and therapeutic vaccine experiments of FIGS. 3A-3D were analyzed by FACS either after 6 hours of stimulation (ex vivo cells) or upon 3 days of incubation with 9 phage-displayed variant epitopes selected at random among 29 clones that showed superior antigenic properties in the T-cell proliferation assays described above, as well as with the FSWT wild-type epitope and the FB22 control epitope.

Figure 4A:
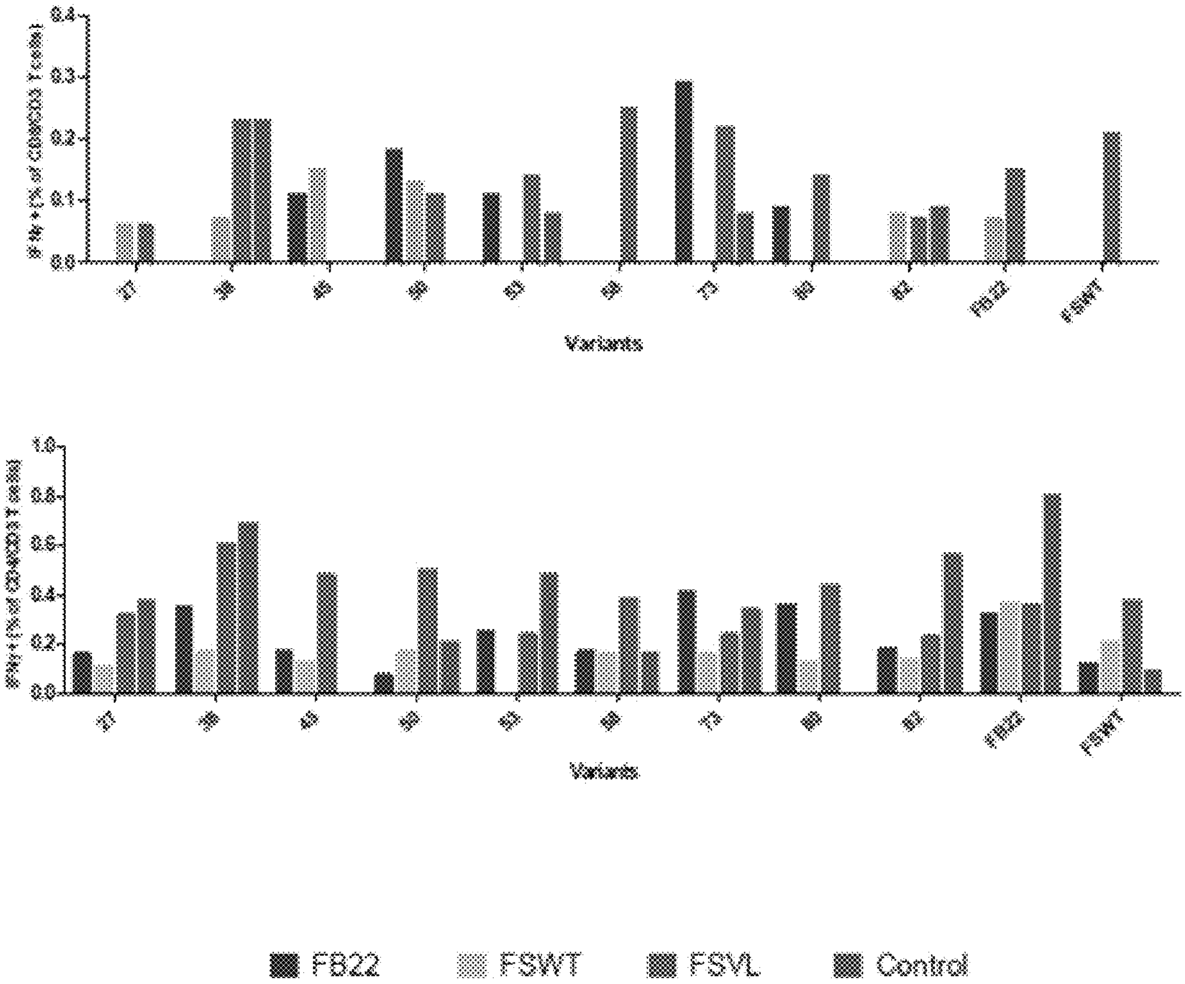
FIG. 4A is a graphical representation of the efficacy of therapeutic administration of specific phage display VEL epitopes to induce activation of subpopulations of T-cells after 6 hours of stimulation with phage clones, according to embodiments herein.
Figure 4B:
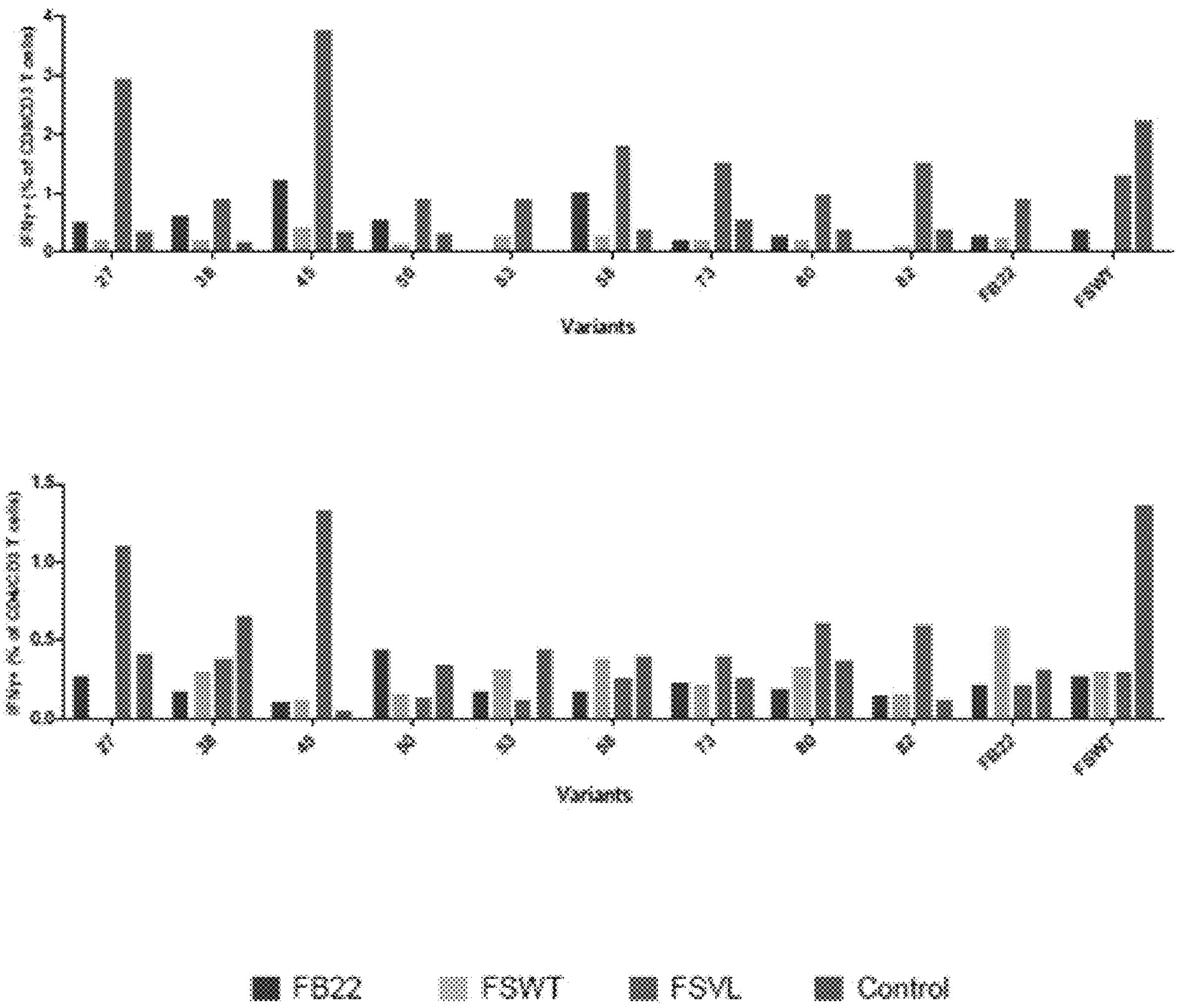
FIG. 4B is a graphical representation of the efficacy of therapeutic administration of specific phage display VEL epitopes to induce activation of subpopulations of T-cells after 72 hours of incubation with phage clones, according to embodiments herein.

In the ICS assays with ex vivo cells in a therapeutic vaccine setting, while the spleen cells collected from mice immunized with FSVL contained only small proportion of IFN-γ-producing CD8+ T cells (about 0.05-0.25%), a several-fold increase in the percentages of epitope variant-specific CD8+IFN-γ+ cells was observed upon stimulation with several clones during a 72 hr. period (48-fold increase for clone 27; 14-fold increase for clone 45; 7-fold increase for clone 58; 6.7-fold increase for clone 73; and a 21-fold increase for clones 82) (FIG. 4A). The incubation of spleen cells with the rest of the epitope variants as well as with the FB22 control epitope resulted in less than about 1% of IFN-γ-producing cells (FIG. 4B). In the example using CD4+IFN-γ+ cells, only clones 27 and 45 were stimulatory against cells from FSVL-immunized mice, exhibiting a 2-3 fold increase in cell percentages.

Figure 4C:
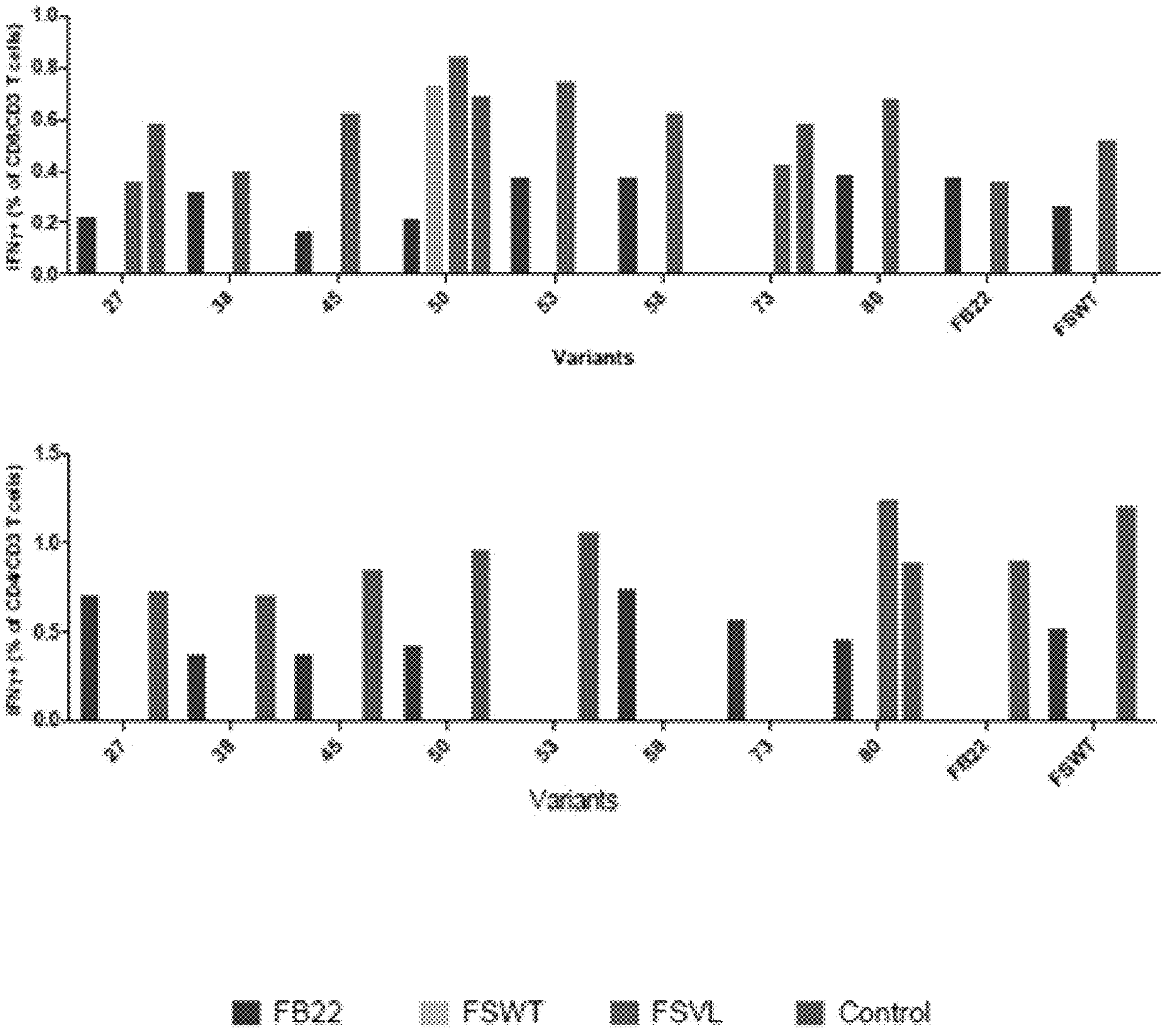
FIG. 4C is a graphical representation of the efficacy of prophylactic administration of specific phage display VEL epitopes to induce activation of subpopulations of T-cells after 72 hours of incubation with phage clones, according to embodiments herein.
Figure 4D:
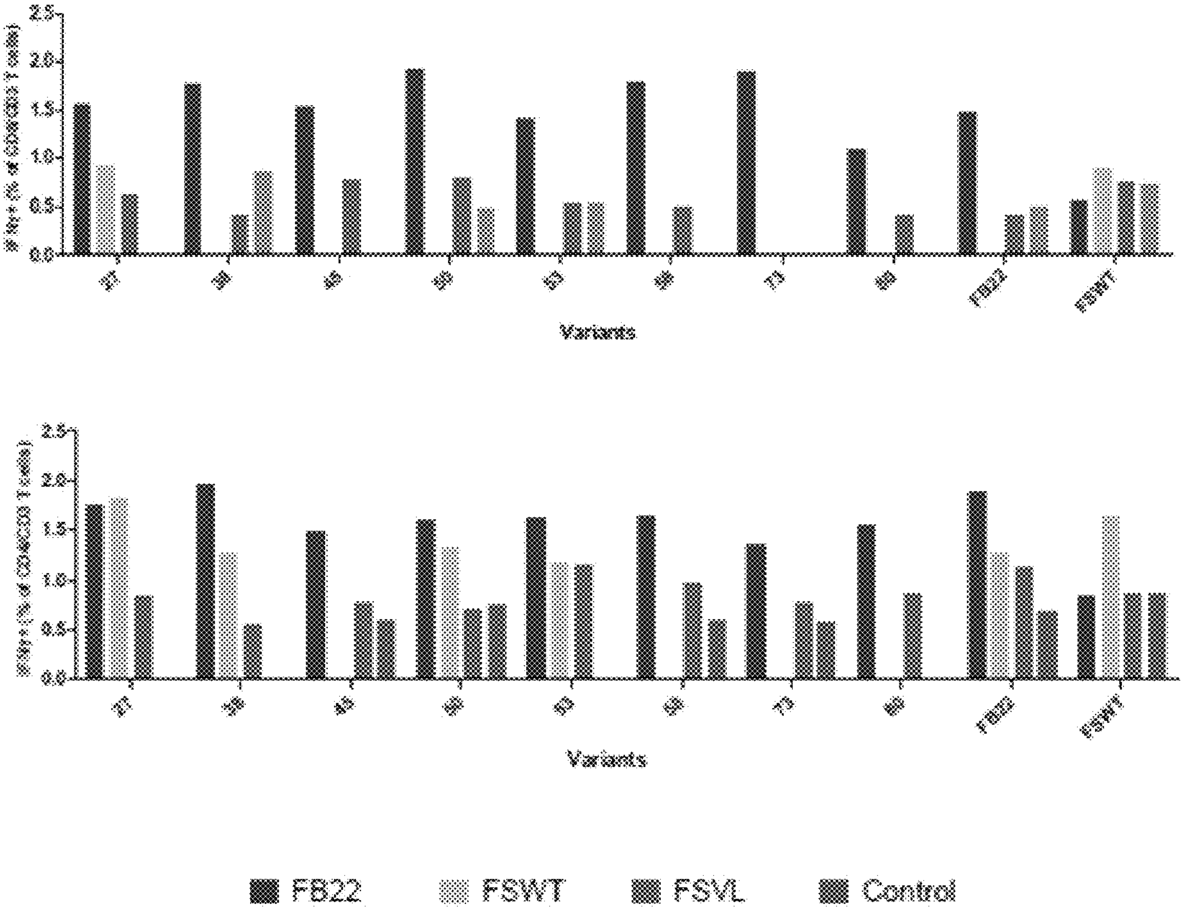
FIG. 4D is a graphical representation of the efficacy of prophylactic administration of specific phage display VEL epitopes to induce activation of subpopulations of T-cells after 72 hours of incubation with phage clones, according to embodiments herein.

In a prophylactic setting, the presence of epitope variant-specific CD8+IFN-γ+ ex vivo cells in FSVL-immunized mice was detected in clones 45, 53, 58 and 80, all of which showed cell percentages above those obtained with the cells from mice immunized with FSWT, FB22 controls, and untreated mice (FIG. 4C). Incubation for 72 hrs. led only to slight increases in cell proliferation, and cell numbers decreased with several epitopes (clones 53, 58, 73 and 80) (FIG. 4D).

Together, these results demonstrate that vaccination with VELs based on a survivin-derived CTL epitope induces both CD4+ and CD8+ effector cytokine-producing T cells and that several variant epitopes lead to increased T-cell proliferation compared to the FSWT epitope.

Example 5

Immunohistochemical Analysis of VEL-Immunized Mice

VEL-immunized mice were also tested to determine whether they exhibited more tumor-infiltrating lymphocytes (TILs) compared to control mice. Tumor tissue sections obtained from mice treated in both prophylactic and therapeutic settings were stained using an anti-CD3 antibody.

More CD3+ cells were observed in the tumors from mice vaccinated by a single inoculation with FSVL 40 days before tumor challenge (prophylactic treatment) compared with mice immunized with FSWT, the FB22 control phage, or with mice transplanted with 4T1 cells without any treatment (data not shown but available upon request). A similar pattern of lymphocytic infiltration was observed in mice vaccinated with the prime/boost regimen (data not shown but available upon request). Also, the presence of TILs was observed in mice vaccinated with corresponding synthetic peptide immunogens, although the general number of CD3+ T cells was lower compared with phage-vaccinated mice (data not shown). These data correlated with tumor challenge studies described above, indicating the possible involvement of these TILs in the anti-tumor effects induced by vaccination with VELs based on a survivin-derived CTL epitope.

Materials and Methods

Variable Epitope Libraries (VELs)

To generate the VELs, molecular biology procedures were carried out using standard protocols, including the use of restriction enzymes, Taq DNA polymerase, DNA isolation/purification kits, T4 DNA ligase and M13KO7 helper phages. In order to express the survivin-derived wild-type CTL peptide epitope GWEPDDNPI (SEQ ID NO. 1) and epitope variant-bearing VELs on M13 phage surfaces as fusions with the major phage coat protein (cpVIII), the corresponding DNA fragments were generated by PCR and cloned in a pG8SAET phagemid vector. Briefly, two oligonucleotides (oligos): 5'-gtat attactgtgcgggttgggaaccagatgataatccaatatggggccagggaacc-3' (SEQ ID NO: 4) and degenerate 5'-gtatattactgtgcgggttgg NNKccaNNK gatNNKccaatatggggccagggaacc-3' (SEQ ID NO: 5), (N is g, a, t or c and, K is g or c nucleotide) were used in two separate PCRs with pair of primers carrying Nco I and Bam HI restriction sites; 5DAMP: 5'-tgatattcgtactcgagccatggtgtatattactgtgcg-3' (SEQ ID NO: 6) and 3DAMP: 5-atgattgacaaagcttggatccctaggttccctggcccca-3 (SEQ ID NO: 7) were used to generate corresponding DNA fragments for their cloning in phagemid vectors using electroporation. Correct sequences were verified using standard automated sequencers.

The resulting recombinant phage clone FSWT expressing the SWT epitope and the phage library carrying SWT-based VELs, referred as FSVL, were rescued/amplified using M13KO7 helper phages by infection of *E. coli* TG1 cells and purified by double precipitation with polyethylene glycol (20% PEG/2.5 M NaCl). Similarly, 87 phage clones randomly selected from the FSVL library, each expressing different epitope variants, were rescued/amplified from 0.8 mL of bacterial cultures using 96 well 1 mL round bottom blocks. The typical phage yields were 1010 to 1011 colony forming units (CFU) per milliliter of culture medium. The DNA inserts of 27 phage clones from the FSVL library were sequenced and the amino acid sequences of the peptides were deduced, as presented in Table 2 below.

TABLE 2

Sequences of survivin-derived epitope variants

| | Wild-type epitope SWT | | | | | | | | |
|---|---|---|---|---|---|---|---|---|---|
| | G | W | E | P | D | D | N | P | I |
| | Epitope Library | | | | | | | | |
| | G | W | $X^a$ | P | X | D | X | P | I |
| Epitope Variants | | | | | | | | | |
| 1 | — | — | F | — | L | — | A | — | — |
| 2 | — | — | L | — | N | — | Y | — | — |

TABLE 2-continued

Sequences of survivin-derived epitope variants

| | Wild-type epitope SWT | | | | | | | | |
|---|---|---|---|---|---|---|---|---|---|
| | G | W | E | P | D | D | N | P | I |
| | Epitope Library | | | | | | | | |
| | G | W | $X^a$ | P | X | D | X | P | I |
| 3 | — | — | R | — | T | — | V | — | — |
| 4 | — | — | F | — | L | — | N | — | — |
| 5 | — | — | I | — | S | — | F | — | — |
| 6 | — | — | Q | — | T | — | E | — | — |
| 7[b] | — | — | T | — | K | — | D | — | — |
| 8 | — | — | D | — | L | — | I | — | — |
| 9 | — | — | Q | — | M | — | S | — | — |
| 10 | — | — | I | — | T | — | A | — | — |
| 12 | — | — | C | — | Y | — | T | — | — |
| 22 | — | — | N | — | S | — | L | — | — |
| 25 | — | — | V | — | T | — | L | — | — |
| 38 | — | — | H | — | L | — | N | — | — |
| 41 | — | — | N | — | F | — | G | — | — |
| 45 | — | — | D | — | L | — | Q | — | — |
| 50 | — | — | A | — | N | — | N | — | — |
| 53 | — | — | V | — | D | — | Y | — | — |
| 58 | — | — | Q | — | V | — | T | — | — |
| 59 | — | — | E | — | T | — | H | — | — |
| 65 | — | — | C | — | Q | — | L | — | — |
| 73 | — | — | W | — | Q | — | E | — | — |
| 79 | — | — | F | — | L | — | V | — | — |
| 80 | — | — | V | — | Y | — | Y | — | — |
| 82 | — | — | R | — | V | — | P | — | — |
| 88 | — | — | T | — | I | — | R | — | — |
| Amino acid frequencies | | | 14/26 | | 12/26 | | 16/26 | | |

[a]X-any of the 20 natural amino acids.
[b]The clones numbered 7, 10, 12, 22, 25, 38, 41, 45, 50, 53, 58, 59, 65, 73, 79, 80, 82 and 88 were used as Ag in T-Cell assays.

The synthetic peptides corresponding to the SWT epitope and the SVL peptide/epitope library, bearing the complexity of $8\times10^3$ individual members, designated as PSWT and PSVL, respectively, as well as a control peptide/epitope library PG5D (A[G/F]PXXXXX[L/M]) with theoretical complexity of $3.2\times10^6$ individual members were prepared using GenScript technology.

Animal Studies

4T1 mouse mammary carcinoma cells (American Type Culture Collection) were maintained for a limited time in vitro by passage in RPMI-1640 medium containing 10% FBS and penicillin (100 U/ml), streptomycin (100 μg/ml) and fungizone (0.75 μg/ml). Groups of 5-7 female 4 to 6 weeks old BALB/c mice were used. To generate breast tumors, mice were injected subcutaneously (s.c.) with 104 viable 4T1 cells in 50 μL of PBS into the right mammary fat pad. Primary tumors were detected by palpation within 1-2 weeks, the mice were observed every 3 days to monitor tumor growth, tumor area was calculated as length×breadth using Vernier calipers and mice were euthanized with CO2 31 days after 4T1 inoculation. For the prevention study, mice were immunized with 5×1012 FSWT, FB22 and FSVL recombinant M13 phage particles (5×1012 CFU) in 200 μL of PBS by intravenous (i.v.) injection into tail vain, and then mice were inoculated with 4T1 cells on day 40 post-vaccination. The tumor growth was monitored as described above. For the established disease study, mice were immunized once with above mentioned phage particles by i.v. injection or with 150 μg of synthetic peptides PSWT, PSVL and PGSD plus 150 μg of polynosine-polycytidylic acid (Poly (I:C)) in 100 μl of phosphate-buffered saline (PBS) by s.c. injection on days 5, 14 and 21 of tumor challenge. In separate studies, the mice primed as described above received 3 (on days 11, 17 and 23 post-tumor cell injection), 2 (on days 17 and 23) or one (on day 26) booster vaccinations with phage or peptide immunogens (5×1011 CFU and 100 μg of synthetic peptides, respectively).

Cell Proliferation Assays

Splenocytes were pooled from 3 animals from each treatment group on day 15 after immunization or tumor challenge and tested using standard flow cytometry protocols. Cells were resuspended in RPMI-1640 medium supplemented as described above plus 1% sodium pyruvate, 1% nonessential amino acids and 1% 2-mercaptoethanol, washed twice with PBS and resuspended at 5×107 cells ml—1 in 5 μM CFSE for 10 min at room temperature. After washing again two times with 10 mL of PBS+5% FBS at 4° C., the cells were stimulated by culturing in a 96-well flat-bottom plate (2.5×105 cells/well) with 1×1010 phage particles/well corresponding to particular epitope variant for 72 hrs. at 37° C. in CO2 incubator. The gating strategy involved exclusion of doublets and dead cells and, 10,000 lymphocytes (R1) were gated for a CD4+ versus CD8+ dot-plot graph to measure CD4+ IFN-γ+, CD8+ IFN-γ+ and proliferation percentages of CD4+CD8− and CD4−CD8+ cells.

Total cell proliferation and CD4+ and CD8+ T-cell responses were evaluated by using intracellular staining (ICS) for IFN-γ both ex vivo and in vitro by stimulating fresh lymphocytes for 6 hrs or 72 hrs, respectively. During the last 4 h, 1 μl well Monensin (2 μM) was added to the culture. The cells were stained with fluorescence-labeled monoclonal antibodies against CD4 and CD8 for 30 min at room temperature, fixed with fixation buffer and, after washing, the cells were permeabilized with permeabilization wash buffer, then labeled for 30 min with anti-IFN-γ antibody in the dark. The cells were analyzed on FACS Calibur Cytometer using CellQuest software; at least 10,000 events were collected Immunohistochemical (IHC) Studies The tumors were removed at day 31 post-tumor injection. The excised tumors were fixed in 4% buffered formalin for 12 hrs. at 40° C. Twenty micrometer-thick free-floating sections were processed using standard protocols. Hydrogen peroxide-quenched and blocked sections were incubated overnight at 4° C. with anti-CD3 primary antibody (Clone 17A2, dilution 1:500). Sections were washed and incubated with HRP Goat anti-rat IgG antibody (dilution 1:800) for 1 hr at room temperature. After multiple washes, color development was performed using a liquid DAB+substrate chromogen system. Samples were placed onto glass slides, stained with hematoxylin, dehydrated with xylene, and covered with Entellan mounting medium. Samples were viewed on Olympus BX51 microscope equipped with an Olympus DP71 digital camera.

Statistical Analysis

All results are expressed as the means±s.e.m. Mouse sample group sizes were at least n=5. All experiments were repeated at least once with comparable results. Tumor size data were analyzed using repeated measurements analysis with Duncan's "post-hoc" test for multiple comparisons. Differences were considered significant at $P<0.05$. Cell proliferation (%) data were analyzed with two tailed t-test. SAS 9.0 software was used for statistical analysis. Proportions of epitope variants were compared using 'z' two tailed test; STATISTICA 8.0 was used in this analysis.

It should also be appreciated that the exemplary embodiment or exemplary embodiments are only examples, and are not intended to limit the scope, applicability, or configuration of the subject matter hereof in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the subject matter hereof as set forth in the appended claims and the legal equivalents thereof.

The embodiments above are intended to be illustrative and not limiting. Additional embodiments are within the claims. Although the present subject matter has been described with reference to particular embodiments, workers skilled in the art will recognize that changes may be made in form and detail without departing from the spirit and scope of the subject matter hereof.

Various modifications to the subject matter hereof may be apparent to one of skill in the art upon reading this disclosure. For example, persons of ordinary skill in the relevant art will recognize that the various features described for the different embodiments of the subject matter can be suitably combined, un-combined, and re-combined with other features, alone, or in different combinations, within the spirit of the subject matter hereof. Likewise, the various features described above should all be regarded as example embodiments, rather than limitations to the scope or spirit of the subject matter hereof. Therefore, the above is not contemplated to limit the scope of the present subject matter hereof.

Other features and advantages of the disclosure will be apparent from the following detailed description, and from the claims.

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed:

1. A method of treating cancer in a subject, the method comprising:

administering a variable epitope library vaccine composition comprising one or more synthetic isolated peptides having amino acid sequences corresponding to an epitope of a tumor antigen that is essential for tumor survival and expressed by said tumor at high levels, or nucleic acid encoding said synthetic isolated peptides, said one or more peptides having from about 7 to about 50 total amino acids, wherein from about 1% to about 50% of the total amino acids of the one or more peptides are variable amino acids, and a pharmaceutically acceptable excipient; wherein the composition generates an immune response when administered to the subject, and wherein said cancer if present in said subject, has a mass of less than 10 $mm^2$, wherein the tumor antigen is survivin comprising a CTL epitope, wherein the survivin CTL epitope is the peptide represented by GWEPDDNPI (SEQ ID NO: 2) having variable amino acids at positions 3, 5 and 7 (GWXPXDXPI (SEQ ID NO: 1)).

2. The method of claim 1, wherein said subject has one or more tumors and wherein said treating the cancer in said subject reduces the size of a said one or more tumors in said subject.

3. The method of claim 1, wherein the cancer is metastatic and capable of immune escape.

4. The method of claim 1, wherein the variable amino acids can be any naturally occurring amino acids.

5. The method of claim 1, wherein the total number of different peptides or in the library is about 87.

6. The method of claim 1, wherein the subject has cancer and wherein the composition is administered to the subject therapeutically.

7. The method of claim 1, wherein the subject has cancer and wherein the composition is administered to the subject therapeutically at a dose from about 100 μg to about 1 mg of isolated peptides.

8. The method of claim 1, wherein the subject has cancer and wherein one or more doses of the composition are administered to the subject therapeutically at weekly intervals.

9. The method of claim 1, wherein the epitope of the tumor antigen is the peptide represented by SEQ ID NO: 1 and wherein the total number of different peptides in the library is about 20 to about 8,000.

10. The method of claim 1, wherein the variable amino acid at position 3 is any of Alanine, Cysteine, Aspartate, Glutamate, Phenylalanine, Histidine, Isoleucine, Leucine, Asparagine, Glutamine, Arginine, Threonine, Valine or Tryptophan.

11. The method of claim 1, wherein the epitope of the tumor antigen is the peptide represented by SEQ ID NO: 1, and wherein the variable amino acid at position 5 is any of Aspartate, Phenylalanine, Isoleucine, Lysine, Leucine, Methionine, Asparagine, Glutamine, Serine, Threonine, Valine or Tyrosine.

12. The method of claim 1, wherein the epitope of the tumor antigen is the peptide represented by SEQ ID NO: 1, and wherein the variable amino acid at position 7 is any of Alanine, Aspartate, Glutamate, Phenylalanine, Glycine, Histidine, Isoleucine, Leucine, Asparagine, Proline, Glutamine, Arginine, Serine, Threonine, Valine or Tyrosine.

13. The method of claim 1, wherein the subject has cancer and wherein therapeutically administering to said subject the variable epitope library vaccine composition comprising peptides represented by GWXPXDXPI (SEQ ID NO: 1), or nucleic acid encoding said peptides, results in an immune response comprising an increased number of CD8+IFN-γ+ cells which recognize variant survivin-derived CTL epitopes than in the immune response resulting from administering peptides represented by GWEPDDNPI (SEQ ID NO: 2), or nucleic acid encoding said peptides.

* * * * *

SEQUENCE LISTING

<160> NUMBER OF SEQ ID NOS: 7

<210> SEQ ID NO 1
<211> LENGTH: 9
<212> TYPE: PRT
<213> ORGANISM: Artificial Sequence -continued
<220> FEATURE:
<223> OTHER INFORMATION: Amino acid sequence derived from a survivin
      CTL epitope
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid

<400> SEQUENCE: 1

Gly Trp Xaa Pro Xaa Asp Xaa Pro Ile
1               5

<210> SEQ ID NO 2
<211> LENGTH: 9
<212> TYPE: PRT
<213> ORGANISM: Artificial Sequence
<220> FEATURE:
<223> OTHER INFORMATION: Amino acid sequence derived from a survivin
      CTL epitope

<400> SEQUENCE: 2

Gly Trp Glu Pro Asp Asp Asn Pro Ile
1               5

<210> SEQ ID NO 3
<211> LENGTH: 48
<212> TYPE: PRT
<213> ORGANISM: Artificial Sequence
<220> FEATURE:
<223> OTHER INFORMATION: Amino acid sequence derived from a survivin
      CTL epitope
<220> FEATURE:
<221> NAME/KEY: MISC_FEATURE
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (20)..(20)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: Xaa can be any naturally occurring amino acid
<220> FEATURE:
<221> NAME/KEY: MISC_FEATURE
<222> LOCATION: (30)..(30)
<223> OTHER INFORMATION: Xaa can be any naturally occurring amino acid
<220> FEATURE:
<221> NAME/KEY: MISC_FEATURE
<222> LOCATION: (32)..(32)
<223> OTHER INFORMATION: Xaa can be any naturally occurring amino acid
<220> FEATURE:
<221> NAME/KEY: MISC_FEATURE
<222> LOCATION: (38)..(38)
<223> OTHER INFORMATION: Xaa can be any naturally occurring amino acid
<220> FEATURE:
<221> NAME/KEY: MISC_FEATURE
<222> LOCATION: (42)..(42)
<223> OTHER INFORMATION: Xaa can be any naturally occurring amino acid
<220> FEATURE:
<221> NAME/KEY: MISC_FEATURE
<222> LOCATION: (48)..(48)
<223> OTHER INFORMATION: Xaa can be any naturally occurring amino acid

<400> SEQUENCE: 3

Ala Gly Phe Ile His Cys Pro Thr Glu Asn Glu Pro Asp Leu Ala Gln

-continued

```
1               5                   10                  15

Xaa Phe Phe Xaa Phe Lys Glu Leu Glu Gly Trp Xaa Pro Xaa Asp Xaa
            20                  25                  30

Pro Ile Glu Glu His Xaa Lys His Ser Xaa Gly Cys Ala Phe Leu Xaa
        35                  40                  45
```

<210> SEQ ID NO 4
<211> LENGTH: 57
<212> TYPE: DNA
<213> ORGANISM: Artificial Sequence
<220> FEATURE:
<223> OTHER INFORMATION: Nucleic acid primer sequence corresponding to a survivin CTL epitope

<400> SEQUENCE: 4
gtatattact gtgcgggttg ggaaccagat gataatccaa tatggggcca gggaacc 57

<210> SEQ ID NO 5
<211> LENGTH: 57
<212> TYPE: DNA
<213> ORGANISM: Artificial Sequence
<220> FEATURE:
<223> OTHER INFORMATION: Nucleic acid primer sequence corresponding to a survivin CTL epitope
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is c or g
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (30)..(30)
<223> OTHER INFORMATION: k is c or g
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (36)..(36)
<223> OTHER INFORMATION: k is c or g
<220> FEATURE:
<221> NAME/KEY: misc_feature
<222> LOCATION: (36)..(36)
<223> OTHER INFORMATION: k is c or g

<400> SEQUENCE: 5
gtatattact gtgcgggttg gnnkccannk gatnnkccaa tatggggcca gggaacc 57

<210> SEQ ID NO 6
<211> LENGTH: 39
<212> TYPE: DNA
<213> ORGANISM: Artificial Sequence
<220> FEATURE:
<223> OTHER INFORMATION: Nucleic acid primer sequence corresponding to a survivin CTL epitope

<400> SEQUENCE: 6
tgatattcgt actcgagcca tggtgtatat tactgtgcg 39

<210> SEQ ID NO 7
<211> LENGTH: 40
<212> TYPE: DNA

-continued

```
<213> ORGANISM: Artificial Sequence
<220> FEATURE:
<223> OTHER INFORMATION: Nucleic acid primer sequence corresponding to
      a survivin CTL epitope

<400> SEQUENCE: 7

atgattgaca aagcttggat ccctaggttc cctggcccca                            40
```